(12) United States Patent
Rana et al.

(10) Patent No.: US 11,850,325 B2
(45) Date of Patent: Dec. 26, 2023

(54) INJECTABLE, BIOADHESIVE CRYOGEL SCAFFOLDS FOR BIOMEDICAL USES

(71) Applicant: Northeastern University, Boston, MA (US)

(72) Inventors: Devyesh Rana, Burlington, MA (US); Sidi A. Bencherif, Boston, MA (US); Nasim Annabi, Los Angeles, CA (US)

(73) Assignee: Northeastern University, Boston, MA (US)

( * ) Notice: Subject to any disclaimer, the term of this patent is extended or adjusted under 35 U.S.C. 154(b) by 352 days.

(21) Appl. No.: 17/080,336

(22) Filed: Oct. 26, 2020

(65) Prior Publication Data

US 2021/0121603 A1  Apr. 29, 2021

Related U.S. Application Data

(60) Provisional application No. 62/925,601, filed on Oct. 24, 2019.

(51) Int. Cl.
| | | |
|---|---|---|
| *A61L 27/26* | (2006.01) | |
| *A61L 27/52* | (2006.01) | |
| *A61K 47/32* | (2006.01) | |
| *A61K 47/58* | (2017.01) | |
| *A61K 47/36* | (2006.01) | |
| *A61K 35/15* | (2015.01) | |

(52) U.S. Cl.
CPC .............. *A61L 27/26* (2013.01); *A61K 35/15* (2013.01); *A61K 47/32* (2013.01); *A61K 47/36* (2013.01); *A61K 47/58* (2017.08); *A61L 27/52* (2013.01); *A61L 2300/204* (2013.01); *A61L 2400/06* (2013.01)

(58) Field of Classification Search
None
See application file for complete search history.

(56) References Cited

U.S. PATENT DOCUMENTS

2014/0227327 A1  8/2014  Bencherif et al.

FOREIGN PATENT DOCUMENTS

WO  WO-2012/149358 A1  11/2012

OTHER PUBLICATIONS

Gizdavic-Nikolaidis et al. The antioxidant activity of conducting polymers in biomedical applications. Current Applied Physics (2004) 4: 347-350. (Year: 2004).*
Bencherif et al. Injectable preformed scaffolds with shape-memory properties. PNAS (2012) 109: 19590-19595. (Year: 2012).*
Wang et al. Mussel-Inspired Conductive Cryogel as Cardiac Tissue Patch to Repair Myocardial Infarction by Migration of Conductive Nanoparticles. Adv. Funct. Mater. (2016) 26: 4293-4305. (Year: 2016).*
Bian et al. A shear-thinning adhesive hydrogel reinforced by photo-initiated crosslinking as a fit-to-shape tissue sealant. J. Mater. Chem. B (2019) 7: 6488-6499. (Year: 2019).*
Rana et al., "Engineering Tissue Adhesive and Injectable Bio-Inspired Cryogel Scaffolds." Presentation at AlChE Annual Meeting. Nov. 1, 2018 (22 pages).
Rana et al., "Engineering an Adhesive and Injectable Cryogel Scaffold" Abstract. AlChE Annual Meeting. Nov. 1, 2018. (17 pages).

* cited by examiner

*Primary Examiner* — Allison M Fox
*Assistant Examiner* — Alyssa G Weston
(74) *Attorney, Agent, or Firm* — Dana M. Gordon; Laura A. Wzorek; Foley Hoag LLP

(57) ABSTRACT

Disclosed herein are functionalized dopamine derivatives comprising an optionally substituted acrylic acid moiety and optionally a polyethylene glycol linking moiety. The functionalized dopamine derivatives are useful in cryogel formulations to improve the adhesivity of the cryogel, while preventing undesirable oxidation typically associated with dopamine-containing hydrogels and cryogels. Properties such as cryogel adhesivity, pore size, and interconnectivity are tunable features. Also provided herein are methods of treating a wound or promoting tissue regeneration with a cryogel of the invention or a formulation comprising such a cryogel.

13 Claims, 11 Drawing Sheets

INJECTABLE, BIOADHESIVE CRYOGEL SCAFFOLDS FOR BIOMEDICAL USES

RELATED APPLICATION

This application claims the benefit of priority to U.S. Provisional Patent Application No. 62/925,601, filed Oct. 24, 2019.

BACKGROUND

Each year in the US millions of hospital visits include invasive, therapeutic surgeries. Despite substantial advances in gelatin, fibrin, and cyanoacrylate-based biomaterial adhesives useful in such procedures, existing biomaterial-based adhesives suffer from problems relating to tissue integration, biomechanical integration, and/or wet-tissue adhesion. For example, gelatin-based adhesives offer robust mechanical properties and biocompatibility but possess poor adhesion to native tissues, and can rapidly degrade and lead to immunological cytotoxicity.[1] Fibrin adhesives have poor adhesion, tensile strength, and their utilization can be allergenic and involve risks of blood-borne disease transmission.[2-5] Cyanoacrylate-based tissue adhesives possess fast crosslinking and robust bond strengths, however they are highly toxic, generating formaldehyde and radicals in both the unpolymerized and polymerized states.[6] Furthermore, secondary biomaterial fixation via sutures or staples can be traumatic for patients.[7-8] There is great interest in minimally invasive surgical techniques using biomaterial-based bioadhesives, which can be easily deployed via flexible mechanical stresses, and which can improve tissue regeneration.

Hydrogels are 3D hydrophilic polymer networks that can absorb a large amount of water while maintaining their structural integrity. Hydrogels made out of synthetic or naturally derived biopolymers, such as gelatin and hyaluronic acid (HA), are considered ideal for tissue engineering applications due to their similarity to native tissues and are widely used in biomedical applications. Hydrogels possess a mesoporous network, but it is more advantageous to use large interconnected pores (i.e., greater than 10 um) to better facilitate cellular infiltration and trafficking. In order to achieve this larger pore size, hydrogels undergo crosslinking at subzero temperatures. This process is referred to as cryogelation. In order to achieve injectability, the biomaterial must pass through a small-bore needle or a catheter. Most injectable hydrogels are delivered in the liquid form and crosslinked in situ, which has its own limitations. Conversely, cryogels are crosslinked externally and subsequently injected; as a result, they are generally mechanically soft.

Extracellular matrices (ECMs) are inherently adhesive and promote tissue and cell adhesion. However, synthetic or semi-synthetic ECM-based three-dimensional (3D) biomaterials for tissue regeneration do not intrinsically adhere to moisture-rich surroundings. In order to overcome this poor adhesive property, the incorporation of naturally-derived mussel-inspired dopamine (DOPA) (or more specifically polydopamine (PDA) once polymerized) has become a promising additive for improving biomaterial adhesion to wet surfaces, specifically tissues. DOPA and PDA have been shown to adhere to both organic and inorganic surfaces and have been incorporated into a variety of polymers including gelatin and hyaluronic acid. However, such materials suffer from susceptibility to oxidation, since DOPA is easily oxidized and continues to oxidize indefinitely. This oxidation reaction produces toxic radicals unless controlled via high concentrations of an antioxidant, specifically glutathione.

Thus, there is a need to develop an injectable, wet-tissue adhesive biomaterial that can be deployed with minimal invasiveness and possesses robust biointegration properties.

SUMMARY OF INVENTION

In certain aspects, the present invention provides a compound, or a pharmaceutically acceptable salt thereof, comprising:
(a) a residue of a bioadhesive molecule; and
(b) a polymerizable moiety;
wherein the residue of the bioadhesive molecule and the polymerizable moiety are covalently linked, optionally through a polymeric linking moiety.

In certain embodiments, the compound comprises:
(a) a residue of dopamine; and
(b) an optionally substituted acrylic acid moiety;
wherein the residue of dopamine and the optionally substituted acrylic acid moiety are covalently linked, optionally through a polymeric linking moiety.

In certain aspects, the compound has the structure of formula (I), or a pharmaceutically acceptable salt thereof:

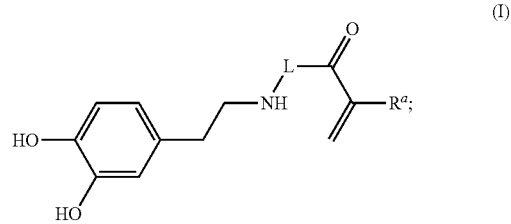

wherein L represents a bond or a polymeric linking moiety; and
$R^a$ represents H, $(C_1$-$C_6)$alkyl, or phenyl.

In other aspects, the present invention provides a cryogel comprising a residue of a compound of the invention; and a hydrophilic bio-compatible polymer.

In further aspects, the present invention provides a formulation comprising a cryogel of the invention and a pharmaceutically acceptable carrier.

Also provided herein is a method of treating a wound, comprising contacting the wound with a cryogel of the invention or a formulation of the invention.

In other aspects, the present invention provides a method of delivering an active pharmaceutical ingredient, biomolecule, or a cell to a tissue, comprising contacting the tissue with a formulation of the invention, wherein the formulation further comprises an active pharmaceutical ingredient, biomolecule, or a cell.

The present invention also provides a method of delivering an active substance to a tissue, comprising contacting the tissue with a formulation of the invention, wherein the formulation comprises an active substance selected from the group consisting of stem cells, immune cells, transplant pre-formed microtissues, DNA, RNA, siRNA, proteins, peptides, steroids, and immunomodulatory factors.

The invention also provides a method of promoting tissue regeneration, comprising contacting a damaged tissue with a cryogel of or formulation of the invention.

DETAILED DESCRIPTION OF THE INVENTION

Figure 1:
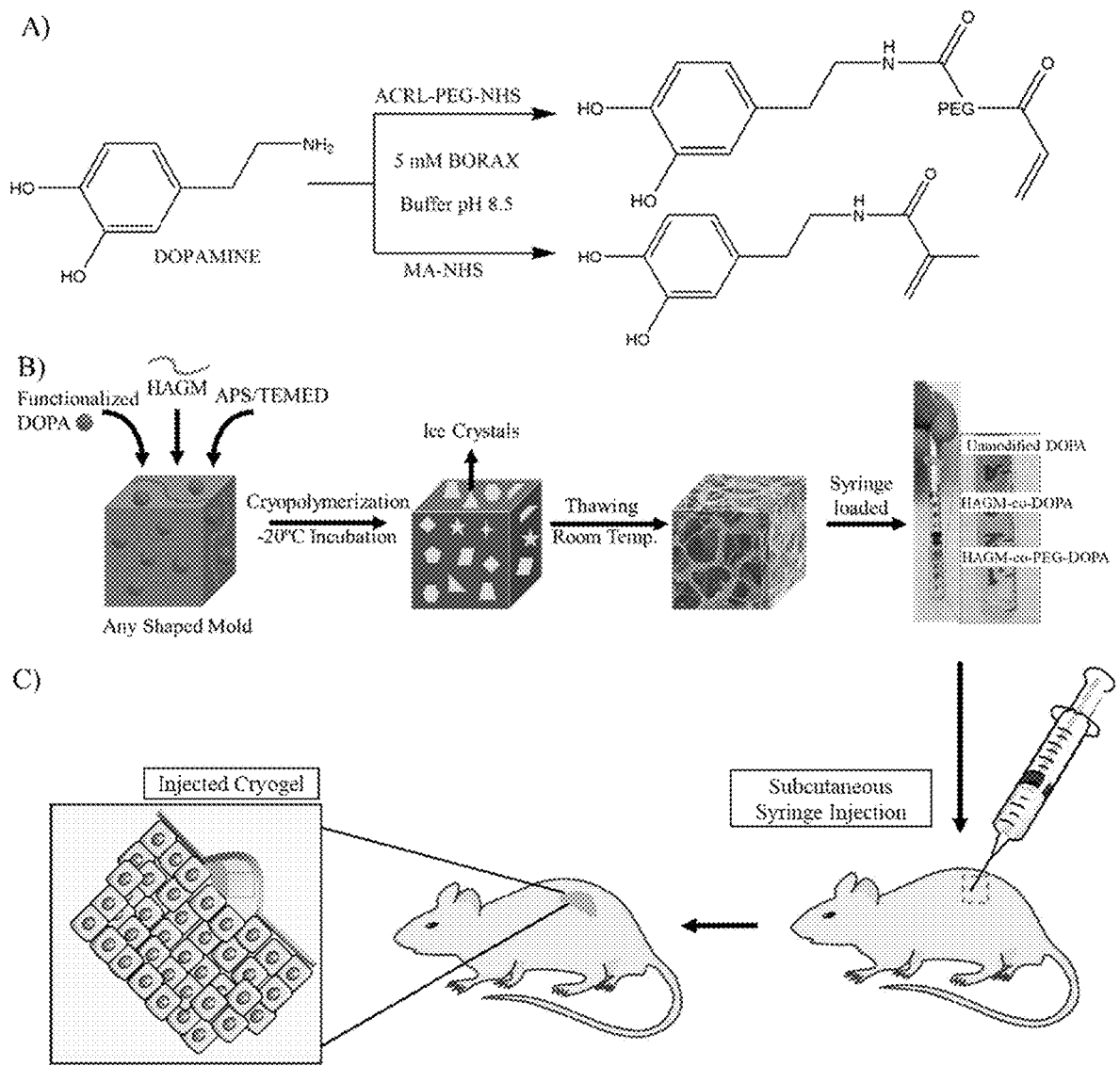
FIG. 1 shows a schematic of dopamine (DOPA) functionalization, polymer conjugation, and minimally invasive surgical procedure of cryogels. Panel A is a scheme showing DOPA functionalization to methacrylate or polyethylene glycol (PEG)-linked-acrylate. Panel B is a scheme showing how functionalized DOPA, along with polymer, is homogenized, with an initiator (Ammonium persulfate (APS)) and a catalyst (tetramethylethylenediamine (TEMED)), and incubated at −20° C. overnight, whereby ice crystals are generated and the polymer mixture is crosslinked. Upon thawing, ice crystals melt and porous scaffolds are left behind. DOPA-conjugated cryogels are then loaded into a syringe for easy injectable surgical procedures. In panel C, syringe loaded cryogels are injected into active wound sites in which cryogels will uptake surrounding fluids and swell to fill the damaged site.

The present invention is based on the surprising discovery that functionalizing the amine-moiety of DOPA prevents undesired oxidation of cryogel biomaterials that incorporate DOPA, thereby mitigating the harmful effects of oxidation. Moreover, functionalization of the amine moiety of DOPA allows for the adhesive properties of the cryogel to be tuned as desired for a particular application.

The cryogels of the invention may generally be formed via cross-linking a hydrogel comprising hyaluronic acid methacrylate (HAGM) or methacrylated gelatin (GelMA) under sub-freezing temperature via free radical polymerization. The cryogel composition of the invention may further comprise chemically bound methacrylated-dopamine (AD) or acrylated-polyethylene glycol linker-dopamine (APD) within the matrix. The cryogel composition, with or without dopamine (DOPA) additives, can be combined into adhesive polymers capable of being compressed to 95%+ of its original volume while retaining its original shape, making them injectable. The cryogel polymers have shape memory properties and can be shaped or polymerized into any shape or size.

The cryogel compositions of the invention thus possess properties of ultracompressibility, a unique macroporous network, injectability, softness, and shape-memory. These properties have advantages for non-invasive deliveries, cavity filling, drug delivery, cell delivery and transplantation, and tissue regeneration. Moreover, the physico-chemical properties of the cryogels of the invention are customizable and tunable. Furthermore, adhesion of the polymers HAGM and GelMA can be improved with the addition of AD and APD, thereby making a preformed injectable bioadhesive cryogel.

Disclosed is a template for an adaptable acrylated-DOPA (AP) or acrylated-PEG-DOPA (APD) precursor which can be conjugated to polymeric biomaterials, such as methacrylated hyaluronic acid (HAGM) or methacrylated gelatin (GelMA), thereby forming conjugated robust adhesive cryogels. Results indicate that the highest wet tissue adhesion is obtained for systems in which PEG-DOPA is conjugated to a biopolymer, as compared to a biopolymer without DOPA, PEG, or PEG-DOPA conjugated segments. Furthermore, there are minimal to no cytotoxic or immunological complications with and without PEG-DOPA conjugated cryogels. Findings highlight the significant improvement in wet-tissue adhesion by the functionalization of DOPA when compared to non-functionalized DOPA. The template for functionalization of DOPA provided herein can be applied to many biopolymers for improved wet-surface adhesion.

For increased adhesion and increased adhesive tunability, described are methods for functionalizing the amine-containing backbone of DOPA. Without being bound to any theory, it is believed that by functionalizing the amine in the DOPA backbone, rapid oxidation is prevented, thereby increasing overall adhesion to wet surfaces, including tissues, when conjugated to biopolymers.

Definitions

The term "residue" as used herein means a portion of a chemical structure that may be truncated or bonded to another chemical moiety through any of its substitutable atoms. As an example, the structure of dopamine is depicted below:

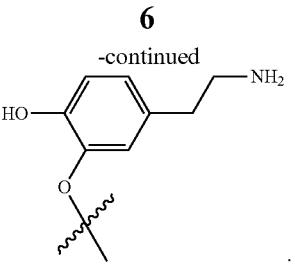

(dopamine)

Residues of dopamine include, but are not limited to, any of the following structures:

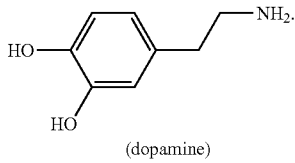,

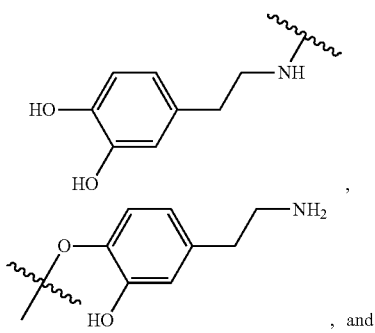, and

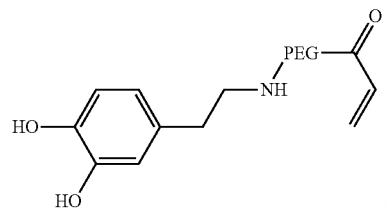.

As another example, an exemplary compound of the invention is depicted below:

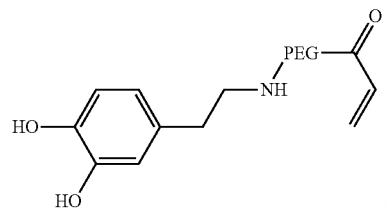

Residues of the compound of the invention, e.g., when the compound of the invention is cross-linked to a bio-compatible polymer to form a cryogel, include, but are not limited to, any of the following structures:

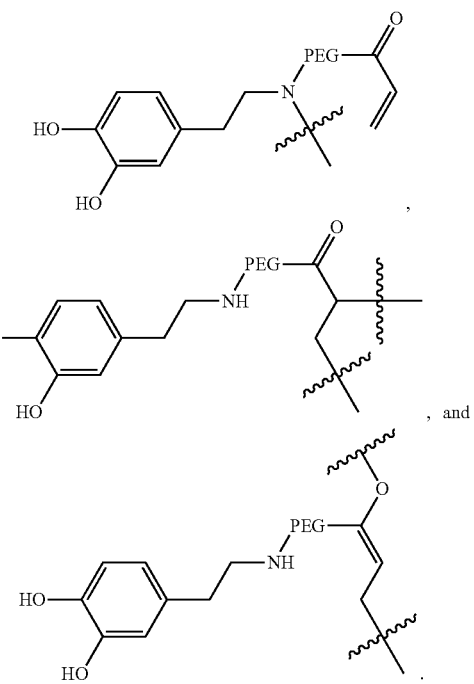

An "alkyl" group is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, isopropyl, n-butyl, sec-butyl, tert-butyl, pentyl, hexyl, pentyl and octyl. A $C_1$-$C_6$ straight chained or branched alkyl group is also referred to as a "lower alkyl" group.

The term "bio-compatible polymer" is used to mean repeating units of biological or chemical moieties that is compatible with a biological system or that mimics naturally occurring polymers. Bio-compatible polymers may be synthetic or naturally derived. Representative bio-compatible polymers include, but are not limited to oligonucleotides, polynucleotides, peptides, polypeptides, proteins, hormones, oligosaccharides, polysaccharides, lipids, glycolipids, lipopolysaccharides, phospholipids, synthetic analogues of the foregoing and combinations of the foregoing. Suitable polymers useful in the method of the invention include hydrophilic bio-compatible polymers. More specifically, suitable polymers and monomers include naturally derived polymers (alginate, hyaluronic acid, chitosan, heparin, cellulose ethers (e.g. carboxymethyl cellulose, cellulose), elastin, gelatin, starch, carob gum, pectin, guar gum, carrageenan collagen, xanthan gum, fibronectin, elastin, albumin, etc.) and synthetic polymers (poly(ethylene glycol) (PEG), PEG-derivatives such as PEG-co-poly(glycolic acid; PGA) and PEG-co-poly(L-lactide; PLA), poly(2-hydroxyethyl methacrylate) (pHEMA), poly-2-hydroxyethylacrylate (polyHEA), PAAm, poly(N-isopropylacrylamide) (PNIPAAm), polyamines and polyethyleneimines, polyvinyl alcohol, polyacrylamides, polyacrylic acid, polymethacrylic acid, and so forth. Exemplary bio-compatible polymers useful in the invention include gelatin, gelatin-based bio-compatible polymers, hyaluronic acid, and hyaluronic acid-based bio-compatible polymers.

The term "crosslinking" or "crosslinked" refers to one or more chemical linkages between a compound and a polymer, two polymers (e.g., two polypeptides), or two different regions of the same polymer (e.g., two regions of one protein).

As used herein, the term "hydrogel" refers to a network of polymer chains (e.g., recombinant proteins) in which water or a solvent acts as a dispersion medium. In some embodiments, hydrogels have tunable mechanical properties which are not possible to achieve with other compositions, such as biofilms. In some embodiments, a hydrogel may be self-healing, in that the hydrogel can be broken apart and put back together. In other words, dried pieces of a hydrogel can be rehydrated and assembled together using the re-hydrated gel as a "glue."

A cryogel, as used herein, refers to a hydrogel that has undergone cross-linking at a temperature below the solvent freezing point (e.g., 0° C. for water).

When used in a polymeric linking moiety, polyethylene glycol can consist of 2 repeat units of ethylene glycol up to 500,000 repeat units of ethylene glycol. The average molecular weight of the PEG moiety may be about 100 Da to about 10,000 Da, about 500 Da to about 5000 Da, about 1000 Da to about 5000 Da, about 2000 Da to about 5000 Da, or about 3500 Da.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by the FDA Office of Biological Standards.

The formulations comprising a cryogel of the invention, which formulations are described hereinbelow, may optionally contain a pharmaceutically acceptable excipient.

As used herein, the term "pharmaceutically acceptable excipient" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable excipients include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

The present invention also contemplates pharmaceutically acceptable salts of the compounds of the invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Embodiments of the Invention

In certain embodiments, the present invention provides a compound, or a pharmaceutically acceptable salt thereof, comprising:

(a) a residue of a bioadhesive molecule; and
(b) a polymerizable moiety;
wherein the residue of the bioadhesive molecule and the polymerizable moiety are covalently linked, optionally through a polymeric linking moiety.

In certain embodiments, the bioadhesive molecule is dopamine (DOPA) or a derivative thereof, tropoelastin, or a mussel foot proteins (e.g., Mfp-1 through Mfp-6).

In certain embodiments, the compound comprises:
(a) a residue of dopamine; and
(b) an optionally substituted acrylic acid moiety;
wherein the residue of dopamine and the optionally substituted acrylic acid moiety are covalently linked, optionally through a polymeric linking moiety.

In certain embodiments, the compound has the structure of formula (I), or a pharmaceutically acceptable salt thereof:

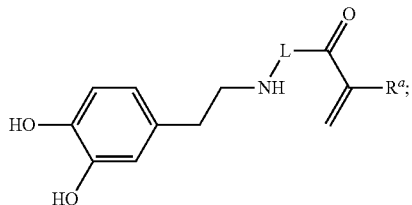

(I)

wherein L represents a bond or a polymeric linking moiety; and
$R^a$ represents H, $(C_1-C_6)$alkyl, or phenyl.

In certain embodiments, $R^a$ represents H. Alternatively, $R^a$ represents $(C_1-C_6)$alkyl, e.g., methyl. In further alternative embodiments, $R^a$ represents phenyl.

In certain embodiments, L represents a bond. Alternatively, L represents a polymeric linking moiety. In certain embodiments, L represents a hydrophilic linear polymeric linking moiety. In still further embodiments, L represents a polyethylene glycol linking moiety.

In certain embodiments, the compound is selected from the group consisting of:

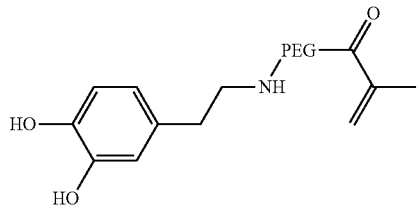

,

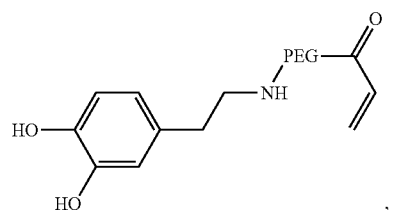

,

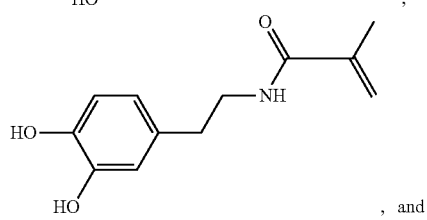

, and

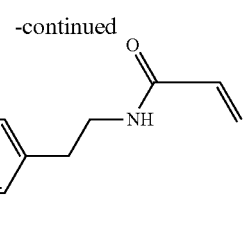

, wherein PEG is a polyethylene glycol linker.

In certain embodiments, the compound is selected from the group consisting of:

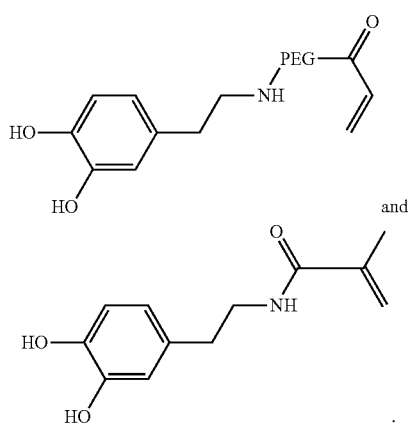

and

In some embodiments, the compound is

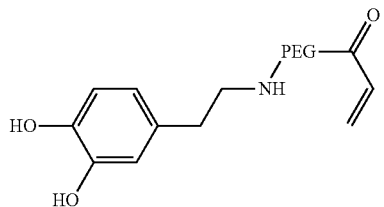

.

Alternatively, the compound is

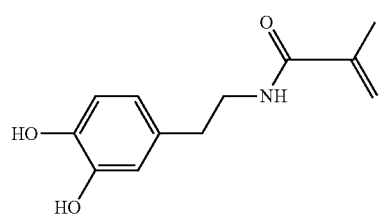

.

In certain embodiments, the present invention provides a cryogel, comprising a residue of
a compound described herein; and
a hydrophilic bio-compatible polymer.

In certain embodiments, the residue of a compound of any one of claims 1-15 is crosslinked to the hydrophilic bio-compatible polymer.

For example, in embodiments in which the compound comprises an acrylate or methacrylate moiety, and the hydrophilic bio-compatible polymer comprises an acrylate or methacrylate moiety, the compound and the hydrophilic bio-compatible polymer may be cross-linked via free-radical polymerization of the acrylate or methacrylate moieties.

In addition to the free radical polymerization process to cross-link the polymers and make chemically cross-linked injectable cryogels, gels are optionally polymerized using other processes. Injectable cryogels can be classified under two main groups according to the nature if their cross-linking mechanism, namely chemically and physically cross-linked gels. Covalent cross-linking processes include radical polymerization (vinyl monomers reaction), Michael-type addition reaction (vinyl-thiol reaction), polycondensation (esterification reaction between alcohols and carboxylic acids or amide formation between carboxylic acids and amines), oxidation (thiol-thiol cross-linking), click chemistry (1,3-dipolar cycloaddition of organic azides and alkynes), Diels-Alder reaction (cycloaddition of dienes and dienophiles), Oxime, Imine and Hydrazone chemistries. Non-covalent cross-linking include ionic cross-linking (e.g., alginate crosslinking with calcium, magnesium, potassium, barium), self-assembly (phase transition in response to external stimuli, such as temperature, pH, ion concentration, hydrophobic interactions, protein-protein interactions, light, metabolite, and electric current).

In certain embodiments, the hydrophilic bio-compatible polymer is selected from the group consisting of a gelatin-based bio-compatible polymer and a hyaluronic acid-based hydrophilic bio-compatible polymer.

In certain embodiments, the hydrophilic bio-compatible polymer is a gelatin-based bio-compatible polymer. e.g., methacrylated gelatin (GelMA).

In certain embodiments, the hydrophilic bio-compatible polymer is a hyaluronic acid-based bio-compatible polymer, e.g., hyaluronic acid methacrylate (HAGM).

In certain embodiments, the concentration of the hydrophilic bio-compatible polymer in the cryogel is about 0.5% wt/v to about 25% wt/v, about 0.5% wt/v to about 10% wt/v, about 2% wt/v to about 6% wt/v, about 3% wt/v to about 5% wt/v, or about 4% wt/v.

In certain embodiments, the concentration of the residue of a compound of the invention is about 0.1 mM to about 5.0 mM, about 0.5 mM to about 3.0 mM, about 1.0 mM to about 2.5 mM, or about 2.0 mM.

In some embodiments, the cryogel further comprises an antioxidant.

Exemplary antioxidants include water-soluble antioxidants, such as ascorbic acid, cysteine hydrochloride, sodium bisulfate, sodium metabisulfite, sodium sulfite, glutathione, and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal-chelating agents, such as citric acid, ethylenediamine tetraacetic acid (EDTA), sorbitol, tartaric acid, phosphoric acid, and the like.

In some embodiments, the cryogel further comprises glutathione.

The present invention also provides methods of making the cryogel of the invention, comprising crosslinking the residue of a compound of the invention and the hydrophilic bio-compatible polymer in a solvent at a temperature below the freezing point of the solvent.

In certain embodiments, the solvent is water.

In certain embodiments, the cryogel compositions are injectable through a hollow hypodermic needle. Upon compression or dehydration the composition maintains structural integrity and shape memory properties, i.e., after compression or dehydration the composition regains its shape after it is rehydrated or the shear forces of compression are removed/relieved. Cryogels can also be introduced into the body via catheter or surgically.

The shape of the cryogel is dictated by a mold and can thus take on any shape desired by the fabricator, e.g., various sizes and shapes (disc, cylinders, squares, cubes, spheres, fibers, strings, foam, etc.) are prepared by cryogenic polymerization. Injectable cryogels can be prepared in the micrometer-scale to centimeter-scale. For instance, cube-shaped (i.e., cubiform) cryogels (4×4×1, 5×5×1, or 10×10×1 mm$^3$) were fabricated and injected through a standard 16G hypodermic needle.

In certain embodiments, the cryogel is biodegradable. For example, the cryogel may be degradable enzymatically, via oxidation, via hydrolysis, and so forth.

The present invention further provides a formulation comprising a cryogel the invention and a pharmaceutically acceptable carrier.

In certain embodiments, the formulation is injectable.

In certain embodiments, the formulation is non-injectable.

In certain embodiments, the formulation further comprises an active pharmaceutical ingredient, a biomolecule, or a cell.

In certain embodiments, the formulation further comprises an active substance selected from the group consisting of stem cells, immune cells, transplant pre-formed microtissues, DNA, RNA, siRNA, proteins, peptides, steroids, and immunomodulatory factors.

Exemplary active pharmaceutical ingredients useful in the formulations of the invention include adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, antihypertensive agents, anti-infective agents, anti-inflammatory agents such as steroids, non-steroidal anti-inflammatory agents, anti-malarials, anti-manic agents, antinauseants, anti-neoplastic agents, anti-obesity agents, anti-parkinsonian agents, antipyretic and analgesic agents, anti-spasmodic agents, anti-thrombotic agents, antiuricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

In some embodiments, the formulation comprises a cell adhesion composition that is chemically linked (covalently attached) to the cryogel. For example, the cell adhesion composition comprises a peptide comprising an RGD amino acid sequence.

The present invention also provides a method of treating a wound, comprising contacting the wound with a cryogel of the invention or a formulation of the invention.

In certain embodiments, the wound is in epithelial tissue. In further embodiments, the wound is in pulmonary tissue. In still further embodiments, the wound is in cardiac tissue.

In certain embodiments, treating the wound comprises closing the wound.

The present invention also provides a method of delivering an active pharmaceutical ingredient, biomolecule, or a cell to a tissue, comprising contacting the tissue with a formulation of the invention, wherein the formulation further comprises an active pharmaceutical ingredient, biomolecule, or a cell.

The present invention also provides a method of delivering an active substance to a tissue, comprising contacting the tissue with a formulation of the invention, wherein the formulation comprises an active substance selected from the group consisting of stem cells, immune cells, transplant pre-formed microtissues, DNA, RNA, siRNA, proteins, peptides, steroids, and immunomodulatory factors.

The invention also provides a method of promoting tissue regeneration, comprising contacting a damaged tissue with a cryogel of the invention or a formulation of the invention.

The advantages of the materials disclosed herein include: improved adhesion to wet surfaces, improved hydrogel implant stability with targeted tissues, improved minimally invasive surgical procedures, and improved tissue regeneration. Moreover, the cryogels of the invention provide a more efficient tissue regenerative material due to their adhesive and biocompatible properties, thereby decreasing the need for repeated surgeries or reapplication. Finally, the improved adhesive properties of the bioadhesive cryogel provide a better interface and integration with tissue surfaces ultimately improving healing time.

The bioadhesive cryogels of the invention may be useful in a number of therapeutic settings, including, but not limited to, soft tissue implantation, cell transplantation, coating of medical devices, reinforcement of another implant, an alternative minimally invasive surgery, and nonsurgical wound care.

In certain embodiments, provided herein is an injectable pre-formed scaffold comprising a cryogel composition of the invention.

In certain embodiments, the bioadhesive cryogels described herein have tunable pore-size and interconnectivity.

In certain embodiments, the bioadhesive cryogels described herein are carriers for drugs or cells.

In certain embodiments, the bioadhesive cryogels described herein is formulated for a bioadhesive drug delivery system. In certain embodiments, the bioadhesive drug delivery system can deliver a controlled release of an active pharmaceutical ingredient.

The present invention provides a scaffold for tissue regeneration or other relevant biomedical applications (e.g., use as a dermal filler, immunomodulation, cell reprograming, etc). The scaffold can deliver pharmaceuticals as well as cells (such as stem cells), DNA, proteins (such as growth factors), peptides, preformed (ex-vivo) microtissues, SiRNA, RNA, steroids, and so forth.

In some embodiments, an injectable cryogel of the invention can be used as a scaffold for cell incorporation. The formed cryogel is mixed with cells to provide tissue engineered products or can be used as a biomatrix to aid tissue repair or tissue augmentation. The incorporated cells can be any mammalian cells (e.g., stem cells, fibroblasts, osteoblasts, chrondrocytes, immune cells).

EXAMPLES

Materials & Methods

Dopamine, glutathione, hyaluronic acid, gelatin, and methacrylic acid NHS were purchased from Sigma-Millipore (Billerica, MA, USA) and used without any further purification. Acrylate-PEG-succinimidyl valerate (MW 3400) was obtained from Laysan Bio, Inc (Arab, AL, USA).

Functionalization of DOPA

In order to obtain acrylate-DOPA (AD) or acrylate-PEG-DOPA (APD) functionalized DOPA molecules, vials, with rubber caps, containing 5 mL distilled water and 25 mg glutathione were initially nitrogen purged for 30 minutes. Following this purge, DOPA and methacrylic acid NHS was quickly added at a 1:1 molar ratio and nitrogen purged again for another 30 minutes. Post-purge, the reaction was placed on a shaker plate to allow the reaction to occur over night. After 24 hours, the resulting solution contained dissolved AD or APD. The solution was then lyophilized to obtain the final product of functionalized DOPA.

Functionalization of Hyaluronic Acid and Gelatin

Methacrylated hyaluronic acid (HAGM) and methacrylated gelatin (GelMA) biopolymers were synthesized as described elsewhere. Briefly, for the preparation of HAGM, A total of 1 gram of hyaluronic acid (Sigma-Aldrich, St. Louis, MO, USA) was dissolved in 200 mL phosphate buffered saline (PBS, Sigma-Aldrich, pH 7.4) and subsequently mixed with 67 mL of dimethylformamide (Sigma-Aldrich), 13.3 g of glycidyl methacrylate (Sigma-Aldrich), and 6.7 g of triethylamine (Sigma-Aldrich). After 10 days of reaction, the solution was precipitated in an excess of acetone, filtered, and dried overnight in a vacuum oven. HAGM was then used without any further processing. Similarly, for the preparation of GelMA, type A porcine skin gelatin was mixed at 10% (w/v) into PBS at 60° C. and stirred until fully dissolved. Methacrylic anhydride was added dropwise under stirred conditions at 50° C. and allowed to react for 1 h. The fraction of lysine groups reacted (degree of methacrylation) was modified by varying the amount of MA present in the initial reaction mixture. Following a 5× dilution with additional warm (40° C.) PBS to stop the reaction, the mixture was dialyzed against distilled water using 12-14 kDa cutoff dialysis tubing for 1 week at 40° C. to remove salts and unreacted excess methacrylic acid. The solution was lyophilized for 1 week to generate a white porous foam and stored at −80° C. until further use.

Preparation of HAGM and GelMA Cryogels

Freeze dried biopolymer (HAGM or GelMA) was used as is or with AD or APD to create HAGM-DOPA (HD) and HAGM-PEG-DOPA (HPD) or GelMA-DOPA and GelMA-PEG-DOPA polymer precursor solutions. To initiate cross-linking, 1% v/v of tetramethylethylenediamine (TEMED) and 2% v/v ammonium persulfate (APS) was added to the precursor solution immediately prior to use. The crosslinker-containing polymer precursor solution was then pipette into preformed Teflon square (4×4×1, 5×5×1, or 10×10×1 mm) or cylindrical (H: 6 mm, D: 8 mm) molds. The filled molds were immediately placed into −20C freezes for 16 hours for the reaction to occur. Finally, polymer scaffolds were removed from molds, followed by wash and storage in PBS prior to use.

Chemical Characterization of Polymers and Cryogels by $^1$H NMR $^1$H NMR analysis was conducted to calculate the degree of methacrylation and assess qualitatively vinyl group consumption during cryogelation using a Varian Inova-500 NMR spectrometer. Deuterium oxide (D2O) was used as solvent, and the concentration of the modified polymers was kept at 1% (w/v). For chemical characterization of the cryogels, cryogelation was induced directly in an NMR tube. One milliliter of the prepolymer solution containing the initiator was transferred into the NMR tube before cryogenic treatment at −20° C. for 16 hours. All $^1$H NMR spectra were obtained at RT, 15 Hz sample spinning, 45° tip angle for the observation pulse, and a 10 second recycle delay, for 128 scans. Peak values at 5.2 and 5.5 ppm for HAGM and at 5.4 and 5.7 ppm for GelMA were correlated to the presence of methacrylated groups. Peak areas were integrated using ACD/Spectrus NMR analysis software and degrees of methacrylation for each polymer type were determined. The degree of methacrylation of HAGM was calculated from the ratio of the relative peak integration of the methylene protons and the peaks correlated to the protons of the main polymer chain.[9,10] For GelMA, the degree of methacrylation, which is defined as the ratio of the number of amine groups functionalized with methacrylamide groups to the total number of amine groups present in gelatin prior to the reaction, can be determined by comparing the integrated intensity of the aromatic region, representing the concentration of gelatin, with the intensity of the double-bond region.[9,11]

Characterization of Adhesion Properties of Cryo gels

Wound closure of the composite cryogels (HAGM, HD, HPD, GelMA GD, GPD), Evicel, and Coseal was calculated by using the ASTM F2458-05 standard[17]. Porcine skin was obtained from a local butcher and cut into small strips (1×2 cm), with excess fat removed. Tissues were immersed into PBS before testing to prevent drying in the air. The tissues were fixed onto two pre-cut poly(methyl methacrylate) slides (20 mm×60 mm) by ethyl 2-cyanoacrylate glue (Krazy glue; Westerville, OH, USA). 6 mm spaces were kept between the slides using the porcine skin. The tissue was then separated in the middle with a straight edge razor to simulate the wound. A 10×10×1 mm rectangular preformed cryogel was placed onto the simulated wound site and then. Samples were then mounted onto an Instron 5542 Mechanical Tester and the entire construct was extended. Maximum adhesive strength of each sample was obtained at the point of tearing at strain rate of 1 mm/min using a mechanical tester (n=5). Data was obtained and analyzed using the Instron's accompanying Bluehill 3 software.

Burst pressure of composite cryogels, Evicel, and Coseal was calculated by using the ASTM F2392-04 standard.[13] Porcine intestine was obtained from a local butcher. Intestine was placed in between two stainless steel annuli from a custom built burst-pressure apparatus, which consists of a metallic base holder, pressure meter, syringe pressure setup, and data collector. A pin-sized hole puncture was made through the intestine and air was flowed using a syringe pump at 0.5 ml/s. The hole made on the intestine was covered with a preformed cylindrical disk shaped cryogel (H: 1 mm, D: 10 mm), prior to initiating the pump and sensor. Airflow was terminated post cryogel rupture and the burst strength (pressure) was recorded (n=5).

Characterization of Mechanical Properties of Cryogels

Cryogels prior to use were incubated for 1 h in DPBS. The subsequent swollen gels were measured using digital calipers. Uniaxial tensile test and cyclic uniaxial compression test were conducted using an Instron mechanical tester. Cryogels for tensile testing were placed between two pieces of double sided tape within tension grips of the instrument, and extended at a rate of 1 mm/min until failure. Elastic moduli were calculated by obtaining the slope of the stress-strain curves. Cryogels for compressive testing were loaded onto compression plates of the instrument under wet conditions, by submerging the plates in a DPBS bath. Cyclic uniaxial compression tests were conducted at a 90% strain level and 1 mm/min strain rate. Cryogels were conditioned cyclically (loading and unloading) for 7 cycles. Post-conditioning, the cryogel underwent a final cycle. Compressive strain (mm) and load (N) were then measured at the 8th cycle using the Instron's Bluehill 3 software. Moduli were determined by obtaining the tangent of the slope of the linear region on the loading stress/strain curve. Energy loss was calculated by obtaining the area between the loading and unloading curves (n=5).

The swelling ratio was determined using a conventional gravimetric procedure. To investigate the swelling ratio of each sample, cylindrical cryogels were prepared and immersed in PBS for 24 h prior to experiment. The equilibrium mass swelling ratio (QM) was calculated by dividing the mass of fully swollen cryogel by the mass of freeze-dried cryogel. The cryogels were washed in deuterated water prior to freeze-drying.

To test degrees of pore interconnectivity, fully hydrated cryogels were first weighed on an analytical scale. Next, a Kimwipe was lightly applied to the scaffolds' surfaces to wick away free water. The weight of partially dehydrated cryogels was recorded again. The degree of pore interconnectivity was calculated based on the amount of water wicked away divided by the initial total amount of water.

To determine pore size and distribution, freeze-dried cryogels (4×4×1 mm) were mounted on SEM sample mount using carbon tape and sputter-coated with platinum/palladium up to 5 nm of thickness. Samples were then imaged using secondary electron detection on a Hitachi S-4800 scanning electron microscope (Hitachi High-Technology Corporation, Tokyo, Japan) while operating at 3 kV and 10 mA. Pore sizes were evaluated using ImageJ software and measuring pore diameters.

Two-Dimensional (2D) Surface Cell Seeding

NIH 3T3 cells were cultured at 37° C. and 5% $CO_2$ in Dulbecco's Modified Eagle Medium (DMEM) media (Gibco), supplemented with FBS (10% v/v) and penicillin/streptomycin (1% v/v). Cryogels (4×4×1 mm) at 4% (w/v) polymer concentrations were used for 2D cultures. 3T3 cells ($2 \times 10^6$ cells/ml) were seeded on the hydrogel. 2D cultures were maintained at 37° C., 5% $CO_2$, and humidified atmosphere.

Cell Viability and Proliferation Assay

Cell viability was determined via a Calcein AM/ethidium homodimer-1 live/dead kit (Genecopeia) according to instructions from the manufacturer. The experiments were carried out one day post-seeding. Fluorescence images were acquired using a Zeiss Axio Observer Z1 inverted microscope and analyzed using ImageJ software. Percent viability was determined as the ratio of viable cells to total number of cells. AlamarBlue cell viability kit (Thermo Fisher Scientific) was used to evaluate metabolic activity (MA) of cells, according to manufacturer protocol. MA was evaluated one day post-seeding. Fluorescence intensity of the resulting solutions was recorded at 535-560 nm excitation and 590-615 nm emission.

Generation of Bone Marrow-Derived Dendritic Cells (BMDCs) and In Vitro Dendritic Cells (DCs) Activation Assay Eight-week-old $C_{57}Bl/6$ mice (The Jackson Laboratory, Bar Harbor, ME, USA) were housed in conventional conditions according to NIH guidelines. All animal experiments were performed in accordance with NIH recommendations, and approved by the DLAM ethics committee at Northeastern University. BMDCs were extracted from C57BL/6 femur bone marrow as described by elsewhere,[14] then cultured for 6 days in RPMI 1640 (Fisher Scientific) supplemented with 10% heat-inactivated FBS, 100 U/mL penicillin, 100 μg/mL streptomycin, 50 μM 2-mercaptoethanol (Fisher Scientific), and 20 ng/mL murine GM-CSF (Genscript, Piscataway, NJ, USA). To evaluate BMDC activation induced by different types of cryogels, cryogels (4×4×1 mm) were incubated with BMDCs in complete culture medium for 1 day (RPMI 1640 supplemented with 10% FBS and 1% penicillin-streptomycin). BMDCs maturation was then evaluated by flow cytometry (BD FACSCalibur DxP upgraded, Cytek Bioscience, Fremont, CA, USA) using the following fluorescent antibodies (Biolegend, San Diego, CA, USA): MHC II (M5/114.15.2, Rat IgG2b, PE/Cy7), CD86 (GL1, rat IgG2a, PE), CD11c (N418, hamster IgG, APC), and CD11b (M1/70, rat IgG2b, κ, APC). Cytokine levels (IL-6, IL-12 and TNF-α) in the cell culture supernatant were analyzed by ELISA (IL12(p70)/TNF-α ELISA MAX Deluxe, BioLegend) according to the manufacturer's instructions. Negative control consists of BMDCs cultured in media alone, while positive control consists of BMDCs incubated in media containing 100 ng/mL of lipopolysaccharide (LPS).

In Vivo Subcutaneous Implantation of Cryogels

All animal experiments were reviewed and approved by Institutional Animal Care and Use Committee (ICAUC; protocol 15-1248R) at Northeastern University (Boston, MA, USA). Male Wistar rats (200-250 g) were obtained from Charles River (Boston, MA, USA) and housed in the local animal care facility under conditions of circadian day—night rhythm and feeding ad libitum. Anesthesia was achieved by isoflurane (2.5%) inhalation, followed by SC buprenorphine (0.02-0.05 mg/kg) administration. After inducing anesthesia, cryogels (4% total polymer concentration (w/v), 4×4×1 mm) were implanted via injection using a sterile 18-gauge needle.

The cryogels sterilized in 70% ethanol (v/v) for 20 minutes and under UV light. Cryogels were loaded into sterile syringes and sterile 18G needles. Cryogels were then injected into subcutaneous pockets along the dorsomedial skin of male Wistar rats. After 21 days post-implantation, animals were euthanized and the cryogels were retrieved along with the surrounding tissues for histological assessment, and placed in cold DPBS. Hydrogels used for biodegradation studies were thoroughly washed in distilled water, and excess tissue was carefully removed under a dissection microscope.

Histological Analysis and Immunofluorescent Staining

After explantation, samples were fixed in paraformaldehyde (4% v/v)) for 4 h, followed by overnight incubation in 30% sucrose (30% w/v) at 4° C. Samples were then embedded in OCT and flash frozen in liquid nitrogen. Frozen samples were sectioned using a Leica Biosystems CM3050 S Research Cryostat. 14-μm cryosections were obtained and mounted in positively charged slides using DPX mountant medium (Sigma). Slides were then processed for hematoxylin and eosin staining (Sigma) according to instructions from the manufacturer. Immunohistofluorescent staining was performed on mounted cryosections as previously reported.[15] Anti-CD3 [SP7] (ab16669), anti-CD206 (ab125212), anti-F480 were used as primary antibodies, and an Alexa Fluor 594-conjugated secondary antibody (Invitrogen) was used for detection. All sections were counterstained with DAPI (Invitrogen), and visualized on an AxioObserver Z1 inverted microscope.

Statistical Analysis

Data analysis was carried out using a 2-way ANOVA test with GraphPad Prism 8.0 software. Error bars represent mean±standard deviation (SD) of measurements ($*p<0.05$, $p<0.01$, and $*p<0.001$, $****p<0.0001$).

Results

Biopolymer-co-DOPA Cryogel Characterization. HA and gelatin-based cryogels intended for fast delivery (minimally invasive) of bioadhesive tissue regenerative scaffolds, were prepared similarly to previously published protocols using methacrylated hyaluronic acid.[16] Functionalization of DOPA was uniquely crafted by the acrylation of DOPA resulting in methacrylated-DOPA (AD) and acrylated-PEG-DOPA (APD), as described elsewhere (FIG. 1 panel A). Methacrylated HA (HAGM), HAGM-co-AD (HD), HAGM-co-APD (HPD), methacrylated gelatin (GelMA), GelMA-co-AD (GD), and GelMA-co-APD (GPD) cryogels were crosslinked via APS & TEMED crosslinking. These cryogel bioadhesives have highly porous and interconnected polymer networks (FIG. 1 panel B). Unlike many of their nanoporous counterparts, they can undergo large deformations and compression without damage allowing them to be injected into subcutaneous tissues. The scaffolds retain their original size and shape due to the polymer's shape memory properties, after injection.[17,18] Furthermore, this ultra-compressiveness highlights its applicability for minimally invasive surgeries (FIG. 1 panel C).

Figure 2:
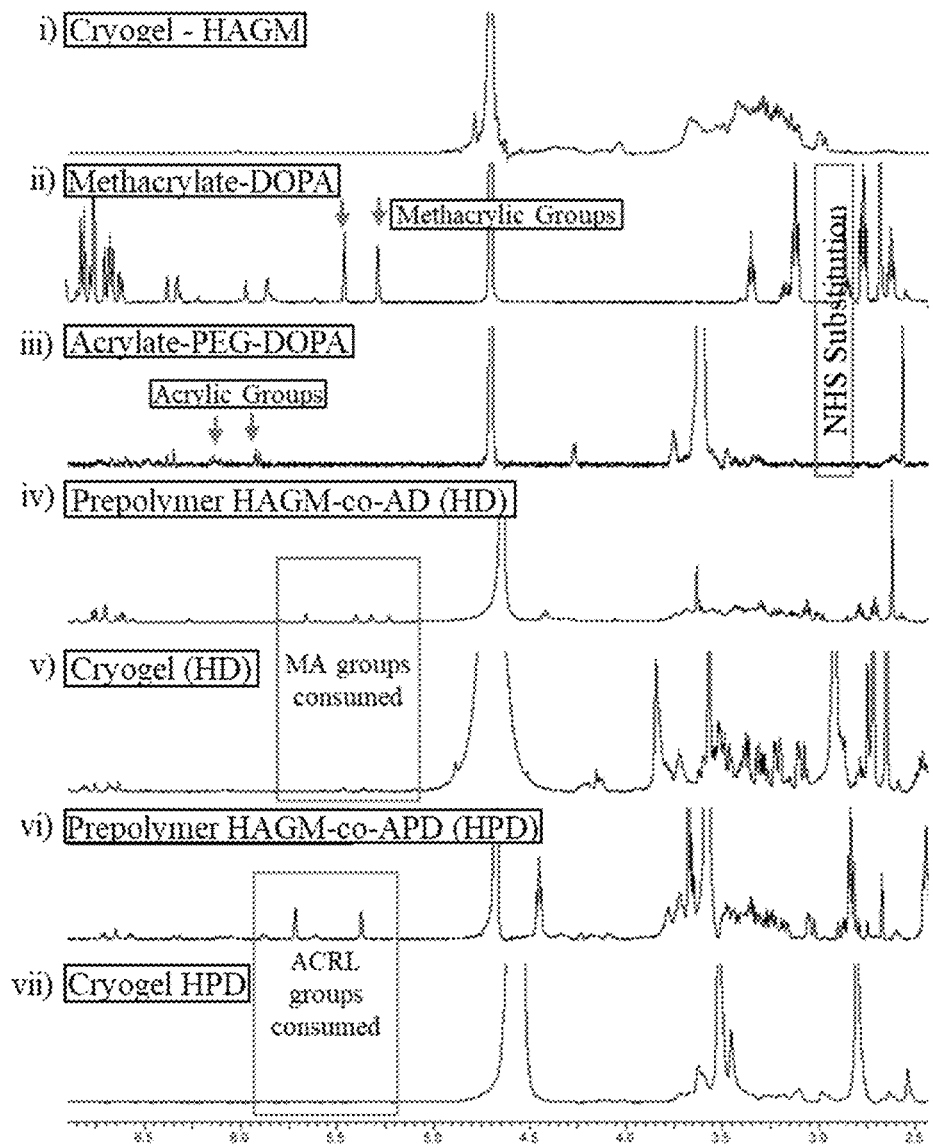
FIG. 2 shows a series of $^1$H NMR spectra in panels (i) through (vii), which show complete consumption of methacrylic and acrylic groups in the formation of HD and HPD cryogels, thus indicating no residual unreacted DOPA or polymer groups. $^1$H NMR of (i) hyaluronic acid methacrylate (HAGM) cryogel (control), (ii) functionalized methacrylated DOPA (AD), (iii) functionalized acrylated-PEG-DOPA (APD), (iv) prepolymer solution of HAGM-co-AD (HD), (v) crosslinked HD cryogel, (vi) prepolymer solution of HAGM-co-APD (HPD), and (vii) crosslinked HPD cryogel.
Figure 3:
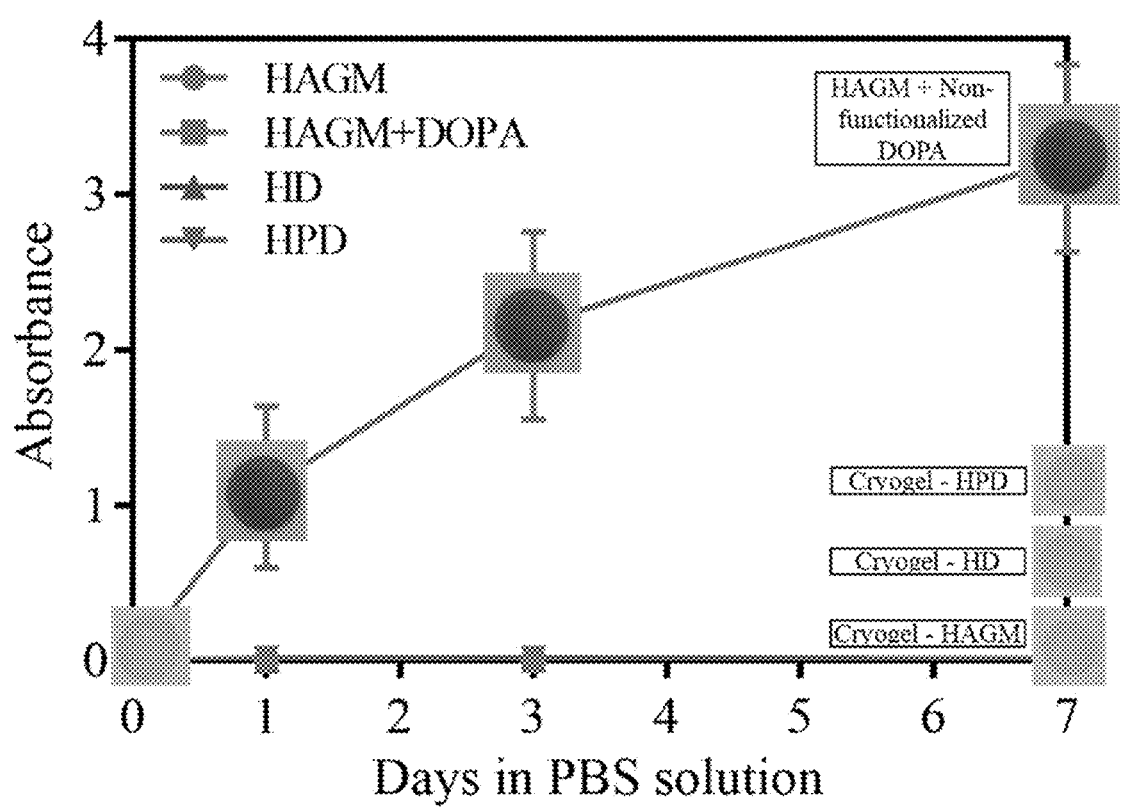
FIG. 3 is a UV-Vis spectroscopy graph showing no residual dopamine oxidation post-crosslinking and 7-day PBS soak for HAGM control, HD, and HPD cryogels. DOPA added directly to HAGM, as in conventional polymer-DOPA gels, shows continued oxidation throughout the 7 days in PBS solution.

The presence of methacrylation and acrylation groups chemically conjugated to HA, gelatin, and DOPA promoted attachment to co-polymers via Friedel-Crafts acylation and to surfaces (including tissues) via integrin binding was observed via 1H NMR. Specifically, an HAGM control cryogel was developed and evaluated for methacrylate shifts at 65.5 and 65.7. This is confirmed by previously published data indicating the disappearance of the methacrylation peaks upon polymerization (FIG. 2 panel i). Next, to correlate the conjugation of methacrylate NHS and acrylate-PEG-NHS to DOPA the disappearance of shifts at 63.0, which correspond to NHS substitution is observed (FIG. 2 panels ii-iii). Next, to confirm the polymerization of HAGM-co-AD, forming HD, the disappearance of methacrylate peaks between 65.3 and 65.6 were evaluated revealing complete crosslinking (FIG. 2 panels iv-v). Similarly, disappearance of acrylate groups revealed complete HPD cryogel crosslinking (FIG. 2 panels vi-vii). Remarkably, it was noticed that the higher the degree of NHS substitution, the less prone to oxidation the end cryogels were revealed to be. Furthermore, this oxidation prevention, which typically manifests as black polydopamine, is consistently prevented in cryogels over time and confirmed via UV-Vis spectroscopy at 520 nm over a 7 day period (FIG. 3).

In vitro adhesion testing on Biopolymer-co-DOPA Cryogels: Wound Closure and Burst Pressure Tests. Various ASTM (American Society for Testing and Materials) standard tests were performed to evaluate the in vitro adhesion properties of HAGM (control), HD, HPD, GelMA (control), GD, and GPD cryogels. Standard wound closure and burst pressure tests were performed on cryogels produced by varying protein concentrations and amount of AD or APD. Furthermore, this was compared to several commercially available biomaterials including fibrin-based Evicel and PEG-based Coseal.

Figure 4:
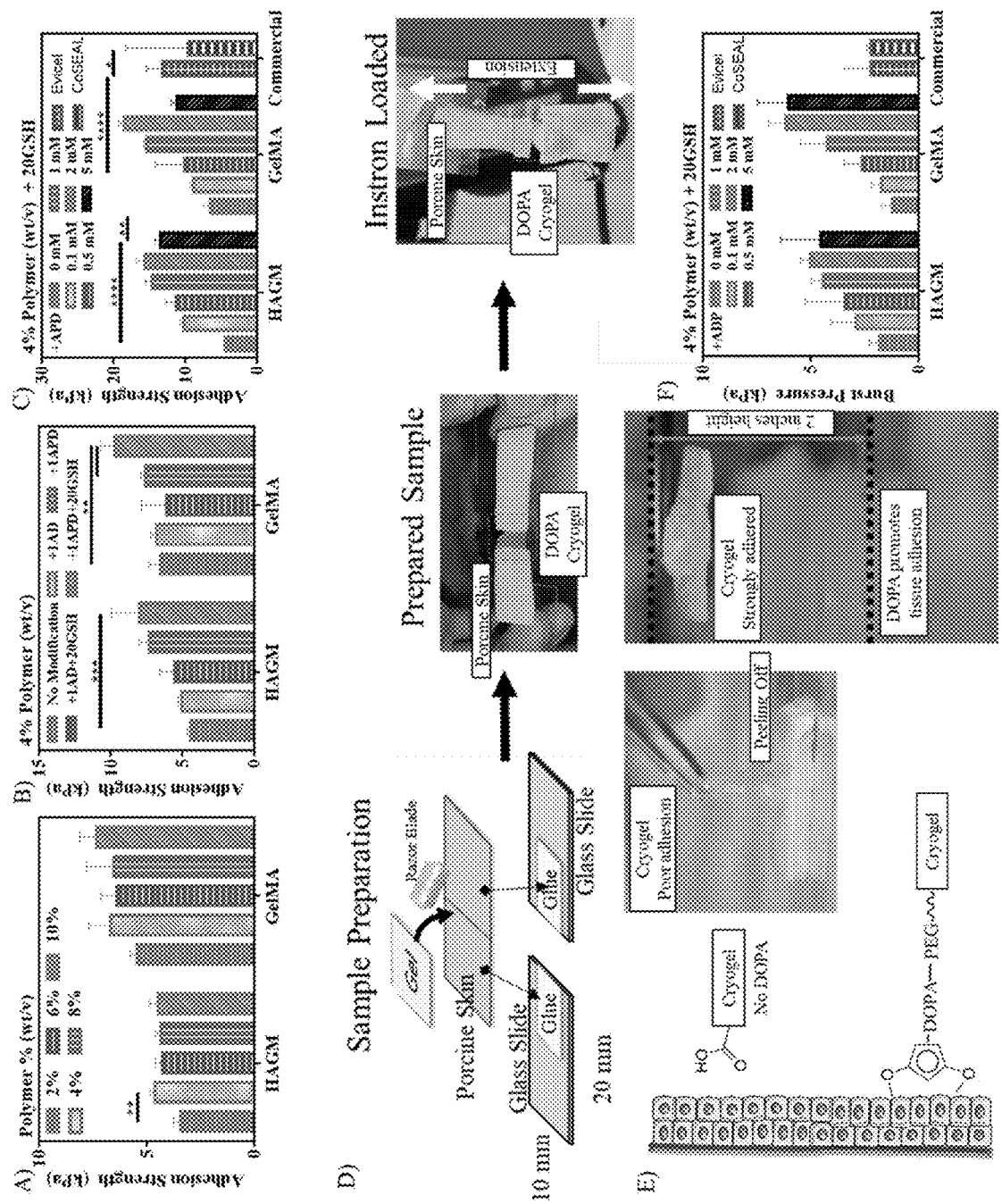
FIG. 4 shows the results of wound closure tests performed to determine the adhesive strength of the engineered cryogels on native tissue (porcine skin) (panels A-C). Panels D and E show schematics of sample preparation and an adhesive peel test. Panel F analyzes the burst pressure using varying concentrations of ADP.

Wound closure tests were performed to determine the adhesive strength of the engineered cryogels on native tissue (porcine skin) according to the ASTM F2458-05 standard (FIG. 4). The adhesive strength of pure HAGM and GelMA cryogels remained fairly static with increasing polymer concentration from 2 to 10% (wt/v) (FIG. 4 panel A). It was also noticeable that concentrations higher than 4% exhibited very high viscosities which required longer times for proper homogenization of polymer in solution, such that overnight homogenization was required. Furthermore, this can be explained by the fact that there are no chemical binding sites on HAGM or GelMA binding to tissue which can be increased by increasing simply protein concentration.[19,20] Specifically, results show HAGM concentration from 2 to 10% (wt/v) resulted in 3.4 to 4.4 kPA adhesion strength, with no significant differences. Similarly, GelMA concentrations from 2 to 10% (wt/v) resulted in adhesion strengths varied from 5.4 to 7.3 kPA, with no significant differences. We next evaluated the ability of AD and APD on adhesion strength with and without 20 mM GSH, antioxidant. Antioxidants, it was found, can improve functionalization-ability and reduce autooxidation thereby consuming binding sites of molecules, as our lab has previously reported. It was found that HD, comprised of 4% HAGM and 1 mM AD, and 1 mM HPD, comprised of 4% HAGM (wt/v) and 1 mM APD, cryogels exhibited 5.2 ±0.2 kPa and 7.3±0.7 kPa adhesion strengths, respectively, compared to 4.4±0.2 kPa HAGM control. Similarly, GD, comprised of 4% GelMA (wt/y) and 1 mM AD, and GPD, comprised of 4% GelMA (wt/v) and 1 mM APD, cryogels exhibited 6.9±0.5 kPa and 7.6±0.3 kPa, respectively, compared to 6.5±0.8 kPa for GelMA control. As had been previously reported by Rana et al, the addition of 20 mM GSH improves the functionalization of DOPA. Therefore, with the addition of 20 mM GSH, an improved adhesion strength was obtained for both HD, HPD. GD, and GPD of 5.5 f 1.1 kPa, 8.0±1.95 kPa, 6.1±1.8 kPa, and 9.7±0.9 kPa, respectively (FIG. 4 panel B). The third optimization varied the ratio of the highest adhesion strength yielding polymers (HPD and GPD) with 20 mM GSH to optimize the amount of APD required for maximum adhesion strength. This was then compared to commercially available Evicel and Coseal. It was found that 2 mM APD, with 20 mM GSH, results in the highest adhesion when conjugated to HAGM or GelMA. HPD and GPD (4% polymer (wt/v) with 2 mM APD) resulted in adhesion strengths of 15.7±1.2 kPa and 18.5±0.8 kPa, respectively. It was also found that higher than 2 mM resulted in decreasing adhesion strength as can be seen by the results of 5 mM APD addition of 13.4 f 0.8 kPa and 11.2±0.8 kPa for HPD and GPD, respectively. We hypothesize that this was a result of an over saturation of DOPA, and can also be observed by the browning of the cryogel post-crosslinking. Our results further show higher or comparable adhesion than commercially available products 13.2±2.3 kPa for Evicel and 9.6±8.7 kPa for Coseal (FIG. 4 panel C). Furthermore, we can compare these results to previously reported data. Specifically, the cryogels reported here possess higher adhesion strengths than chitosan with (1.8 kPa) and without (0.3 kPa) DOPA cryogels. HA with (6-7 kPa) and without (0.8-1 kPa) DOPA hydrogels, and alginate with (3.5-14 kPa) and without (0.38 kPa) DOPA hydrogels. This highlights the significant decrease in adhesion strength just by adding DOPA, without functionalization. As had been previously reported, the simple addition of DOPA causes autooxidation into PDA which results in the consumption of potential binding sites because of PDA formation and conformations.[21] It was also found in previously reported research that DOPA containing materials in conjunction with polyurethane hydrogels and polyethylene glycol hydrogels and cryogels all significantly lost adhesion strength with the incorporation of DOPA. This is in stark contrast to the readily accepted notion that adding DOPA increases adhesion. A summary of adhesion strengths of various materials can be found in Table 1. Finally, a schematic of the wound closure test can be found on FIG. 4 panel D and adhesive peel test on FIG. 4 panel E.

TABLE 1

Summary of bioadhesive strengths of various synthetic and natural biopolymers.

| Material Type | Base Material | Gel type | Adhesion Strength (kPa) | |
|---|---|---|---|---|
| | | | No DOPA | with DOPA |
| Synthetic | Polyurethane | Hydrogel | 110-2480 | 2-10 |
| | | Cryogel | NR | ND |
| Synthetic | Polyethylene Glycol | Hydrogel | 40-60 | 2-8 |
| | | Cryogel | 80-399 | 0.010-0.052 (200-700) |
| Natural | Gelatin | Hydrogel | 30-50 | 10-200 |
| | | Cryogel | 5-7* | 10-20* |
| Natural | Tropoelastin | Hydrogel | 40-70 | ND |
| | | Cryogel | NR | NR |
| Natural | Hyaluronic Acid | Hydrogel | 0.8-1 | 6-7 |
| | | Cryogel | 4-5* | 10-17* |
| Natural | Chitosan | Hydrogel | 2.84-6.98 | 50-450 |
| | | Cryogel | 0.3 | 1.8 |
| Natural | Alginate | Hydrogel | 0.38 | 3.5-14 |
| | | Cryogel | NR | ND |

NR—No adhesion data reported.
ND—No research on this combination has ever been published, as far as we know.
*Data conducted and reported herein.

In vitro burst pressure testing based on the ASTM F2392-04 standard was performed using wet collagen sheet as substrate to determine the ability of the engineered materials to seal tissues under air or liquid pressures. The burst pressure of varying concentrations of APD from 0 mM to 5 mM conjugated to HAGM and GelMA resulted in a similar trend to wound closure (FIG. 4 panel F). Specifically, HPD and GPD consisting 2 mM APD resulted in 5.0±0.4 kPa and 6.1±0.8 kPa, respectively. Similarly, HPD and GPD consisting of 5 mM APD resulted in 4.5±1.8 kPa and 6.0±1.4 kPa, respectively. Comparatively. Evicel and Coseal resulted in burst pressures of 2.2±1.2 kPa and 2.2±0.2 kPa, respectively. HPD and GPD with 2 mM and 5 mM APD resulted in higher burst pressure values than commercially available products Evicel and Coseal ranging from 170% to 640%, supporting its suitability for an improved bioadhesive.

Both of these properties, holistically, are particularly beneficial for injectable tissue adhesives to fully attach to tissue defect surfaces and bind them together for improved tissue integration and eventual defect healing. As an example, these properties show the ability to withstand high pressures occasionally exerted on pulmonary tissue during invasive mechanical ventilation, i.e. by recruitment maneuvers. In this scenario, pressure values can reach up to 40 cm $H_2O$ of intra-alveolar peak pressure (3.9 kPa)[22]—which is not attainable by commercially available products, highlighted above.

Figure 5:
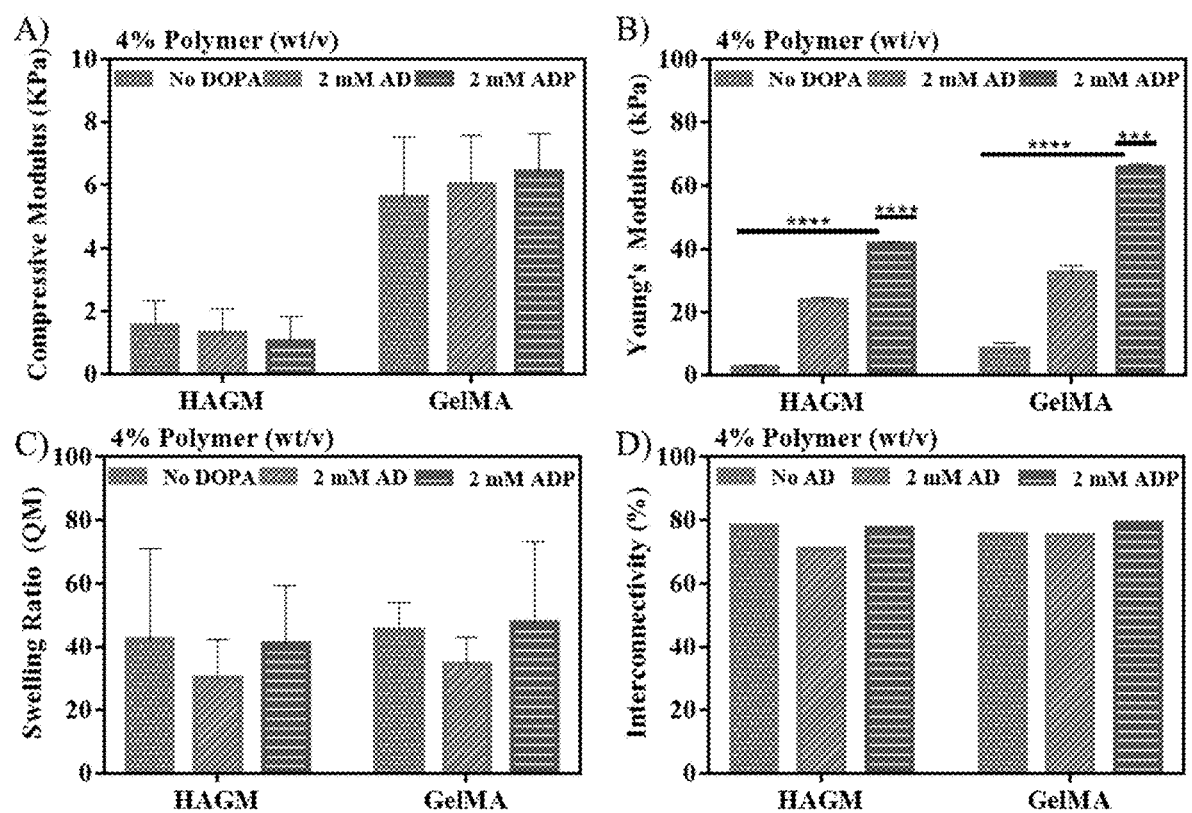
FIG. 5 is a series of bar graphs showing mechanical & physical characterization of HAGM and methacrylated gelatin (GelMA) cryogels conjugated with optimized 2 mM AD or 2 mM APD supplemented with 20 mM glutathione (GSH) showing no change in properties with and without DOPA. Panel A shows compressive modulus, Panel B shows Young's modulus, Panel C shows the swelling ratio, and Panel D shows the interconnectivity with and without DOPA. Data is representative of mean of at least 3 separate experiments ±standard deviation. p<0.0001.

Physical characterization of optimized HAGM, HD, HPD, GelMA, GD, and GPD, Biopolymer-co-DOPA, Cryogels: Compressive Modulus, Young's Modulus, Swelling Ratio, and Pore Interconnectivity. The mechanical properties of optimized HPD and GPD cryogels were evaluated and compared with HAGM (control), GelMA (control), HD, and GD cryogels (FIG. 5). Specifically, important mechanical properties such as compression (FIG. 5 panel A), extensibility (FIG. 5 panel B), swelling (FIG. 5 panel C), and pore interconnectivity (FIG. 5 panel D) were measured. Optimized parameters previously defined were utilized for the comparison: 4% polymer concentration with 20 mM GSH in the prepolymer solution using 2 mM AD or APD. As such, compressive properties of HAGM (control), HD, and HPD resulted in 1.5±0.8 kPa, 1.3±0.8 kPa, and 1.1±0.8 kPa, respectively. Similarly Gel MA (control), GD, and GPD resulted in 5.6±1.9 kPa, 6.0±1.5 kPa, and 6.4±1.2 kPa, respectively (FIG. 5 panel A). It can be observed that with and without acrylated DOPA, compression is unaltered. Moreover, due to the inherent properties of cryogels and how they are made, all cryogels can be compressed up to 90% of their original volume. This is a critical property which allows for passage via a syringe for minimally invasive procedures. Furthermore, Young's modulus is greatly improved with the addition of AD, and is further improved with APD (FIG. 5 panel B). Specifically, Young's modulus of HAGM (control), HD, and HPD resulted in 2.3±0.8 kPa, 23.6+1.0 kPa, and 41.6±0.8 kPa, respectively. Similarly, for GelMA, GD, and GPD resulted in 8.3±1.9 kPa, 32.4±2.3 kPa, and 65.6±1.2 kPa, respectively. This highlights the largely beneficial natures of the addition of AD or APD to biopolymers to improve Young's modulus.

Cryogel network microstructure were also subjected to swelling measurements. HAGM based cryogels exhibited similar swelling ratios regardless of AD or APD conjugation. Specifically. HAGM (control), HD, and HPD cryogels resulted in swelling ratios of 42.5±28.5, 29.9±12.4, and 40.9±18.5. Similarly GelMA based cryogels exhibited similar swelling ratios with and without AD or APD. Specifically, GelMA, GD, and GPD cryogels resulted in swelling ratios of 45.3±8.8, 34.5±8.5, and 47.6±25.5 (FIG. 5 panel C). The consistent swellability suggests the fine control of pore size creation using cryogelation, regardless of biopolymer of composition. Finally, pore interconnectivity was assessed. HAGM and GelMA control cryogels resulted in 77.9±0.1% and 75.4±0.1% pore interconnectivity. HD, HPD, GD, and GPD cryogels resulted in similar pore interconnectivities ranging from 71% to 79%, highlighting the integrity of cryogelation (FIG. 5 panel D).

Figure 6:
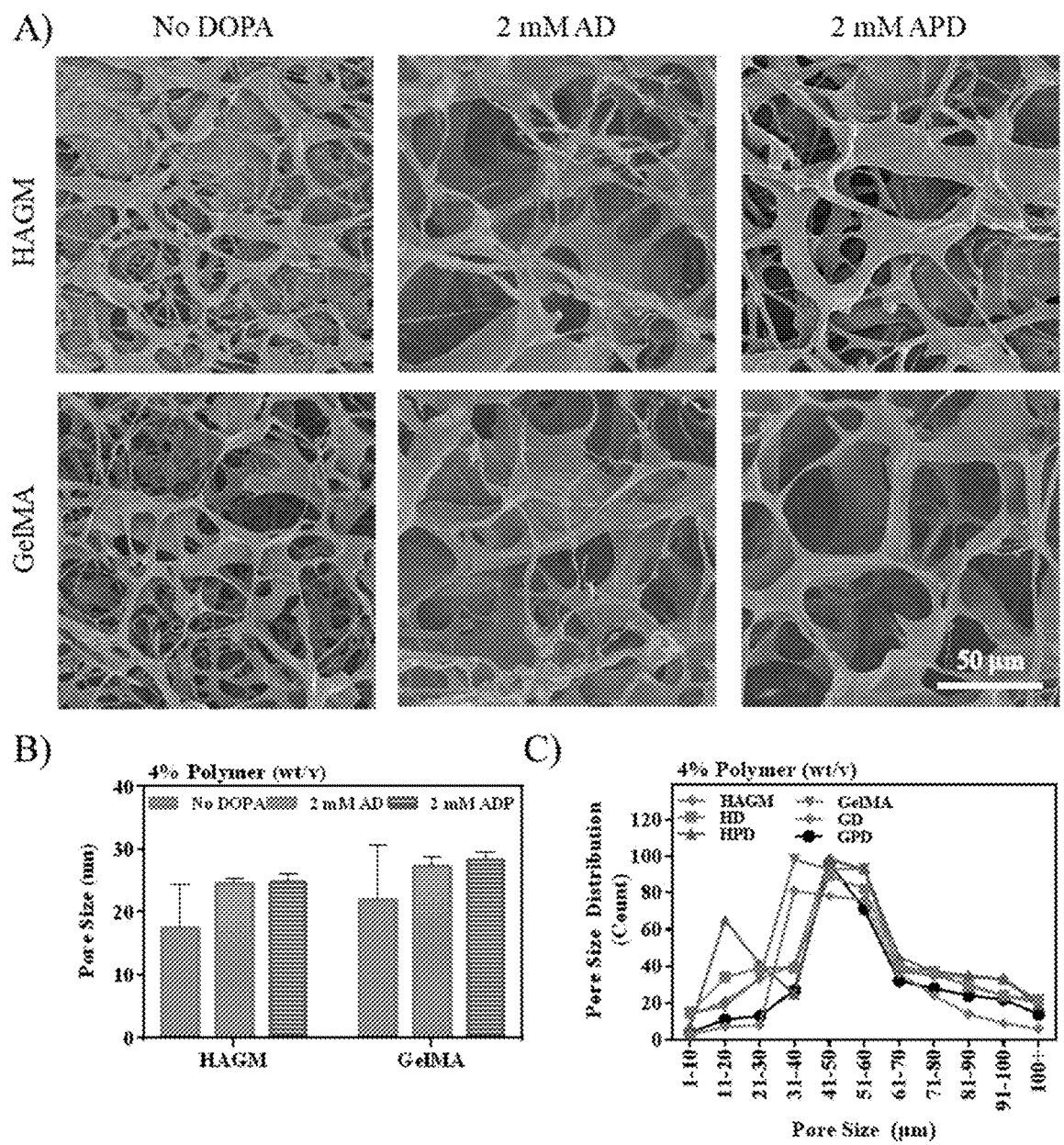
FIG. 6 shows pore size and pore size distribution of HAGM and GelMA cryogels with and without DOPA, indicating no loss of pore interconnectivity or high porosity. Panel A contains representative SEM images of HAGM and GelMA cryogels with and without DOPA. Panel B shows a determination of pore size of HAGM and GelMA cryogels conjugated with and without DOPA. Panel C shows the pore size distribution of HAGM and GelMA cryogels with and without DOPA. Data is representative of mean of at least 3 separate experiments ±standard deviation. p<0.0001.

A typical feature of cryogelation is the ability to produce a system of interconnected macropores, and the microstructure of HAGM, HD, HPD, GelMA, GD, and GPD cryogels was evaluated by various microscopic observations. SEM demonstrated (FIG. 6 panel A) pore sizes in the range of 10-30 µm 9 (FIG. 6 panel B). Comparatively, overall pore size distribution when evaluating entire 10×10×1 mm cryogels, revealed pore sizes ranging from 1 to over 100 µm, with maximum number of pores in the range of 30 to 70 µm (FIG. 6 panel C).

In vitro cytocompatibility and biocompatibility of the optimized cryogels. The optimized HAGM and GelMA cryogels created with 20 mM GSH, 4% polymer concentration with and without 2 mM AD or APD were then evaluated for cytotoxicity. The engineered cryogels could support the growth and proliferation of NIH 3T3 mouse fibroblasts and dendritic cells (DCs) as model cells, confirming the in vitro cytocompatibility and biocompatibility of engineered cryogels.

Figure 7:
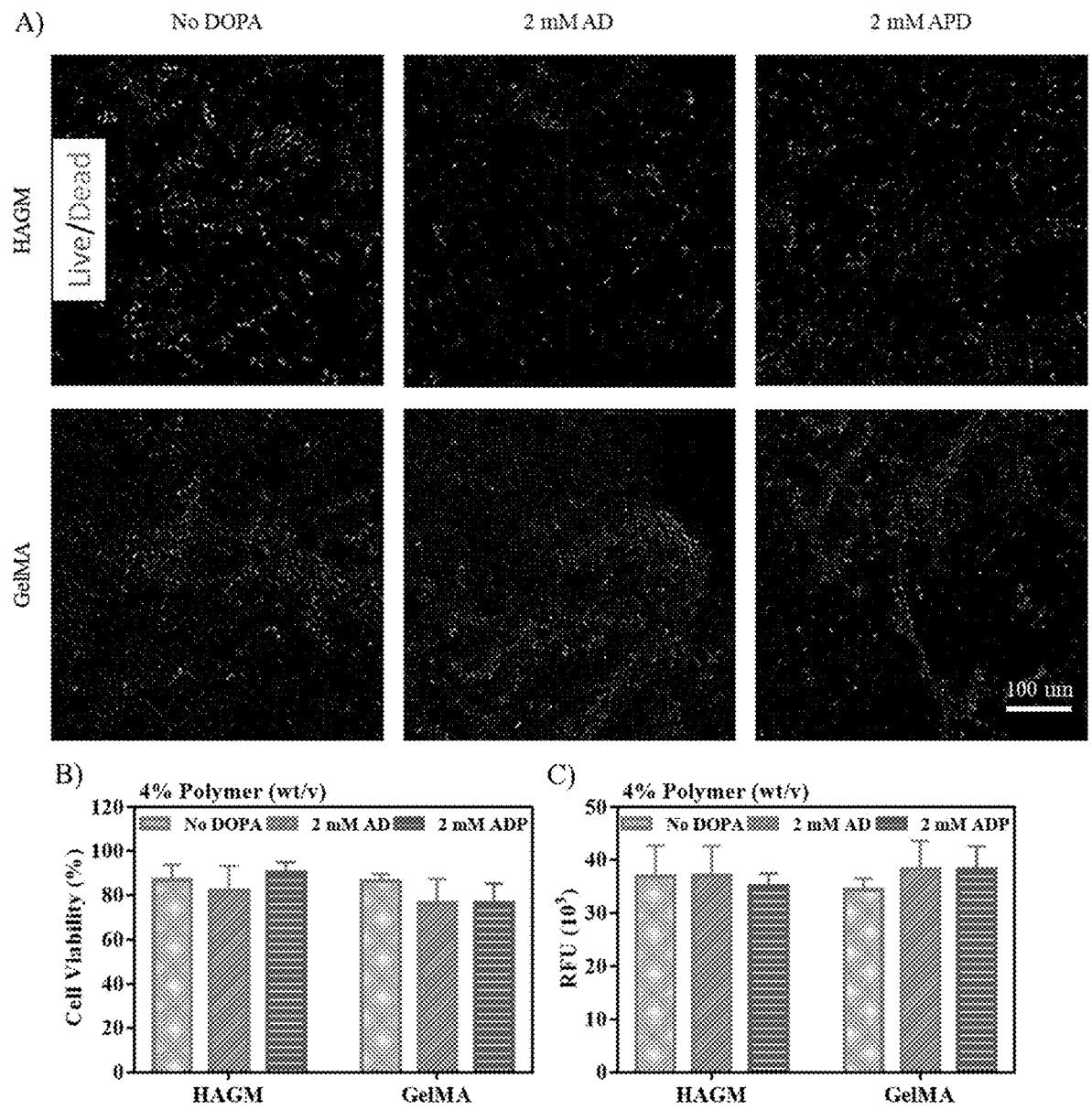
FIG. 7 demonstrates that HAGM (control), HD, HPD, GelMA (control), GelMA-co-AD (GD), GelMA-co-APD (GPD) cryogels comprising 4% total polymer concentration (wt/v) and 2 mM AD or APD showed consistently high cytocompatibility of 3T3 fibroblasts. Panel A contains representative live/dead (Calcein AM/Propidium Iodide) stained images via fluorescent microscopy of 3T3 cells cultured in complete media (DMEM+10% FBS+1% P/S) on HAGM and GelMA cryogels with and without AD and APD. Panel B is a bar graph showing quantification of 3T3 cell viability via Live/Dead stained cells and Panel C is a graph showing Alamar Blue assay indicating 3T3 cell metabolic activity. Data is representative of mean of at least 3 separate experiments ±standard deviation. p<0.0001.

3T3 fibroblasts were cultured on the surface of the cryogels for 5 days. Cell viability and activity were studied. Cell viability was higher than 80% for all seeded conditions suggesting that the cryogels are not cytotoxic (FIG. 7 panels A-B). As can be observed, the cells had adhered to the cryogel, as identified by F-actin cell filament nuclei staining. By day 5 it can also be observed the morphology of cell spreading. The metabolic activity of the cells was quantified by an AlamarBlue assay, which showed a consistency of relative fluorescence intensity across all conditions indicating no loss of metabolic activity despite differences in cryogel composition (FIG. 6 panel C). These results collectively demonstrate the capacity of the cryogels to serve as a biocompatible bioadhesive that promotes cell adhesion, growth, and proliferation.

Figure 8:
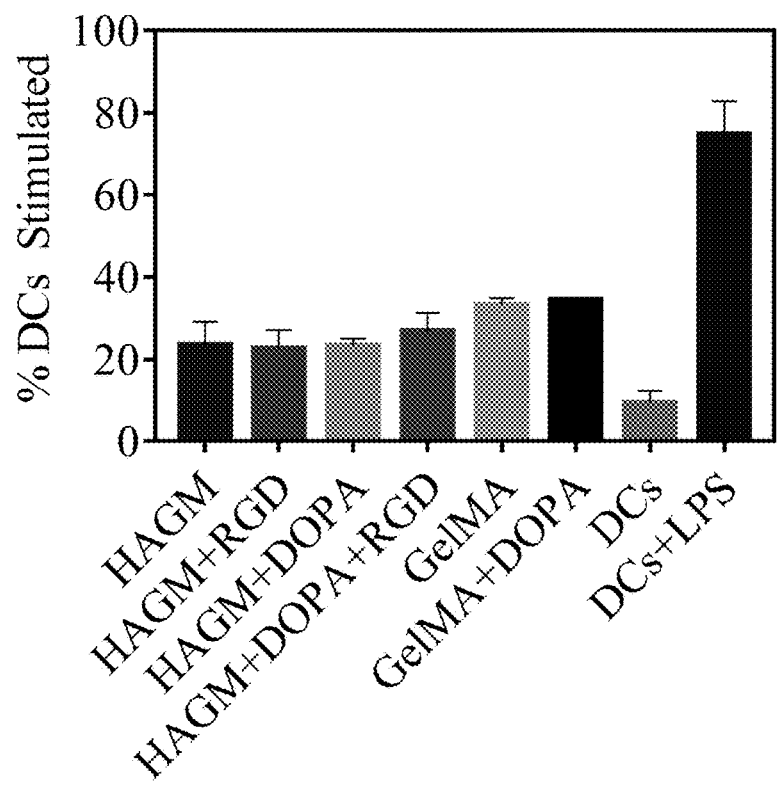
FIG. 8 is a bar graph showing that cryogels comprising 4% total polymer concentration (wt/v) and 2 mM AD or APD revealed low dendritic cell (DC) activation, especially for HAGM, HAGM-RGD (HR), HD, and HAGM-DOPA-RGD (HDR) cryogels, wherein RGD is arginylglycylaspartic acid, the most common peptide motif responsible for cell adhesion to the extracellular matrix. Cryogels of various compositions were introduced to DCs in complete media for 24 hours. DC activation was monitored via expressions of CD86 and MHCII after CD11c and CD11b gating. DCs with (positive) and without (negative) lipopolysaccharide stimulation were used as control.

However, dendritic cells elicited higher stimulation from gelatin-conjugated samples compared to HA-conjugated samples (FIG. 8). This coincides with previous published data suggesting immunological response due to gelatin biodegradation. Therefore final in vivo studies were conducted using simply HAGM (control) and HPD cryogels. At this stage, HD samples were also filtered out due to their lower adhesive strengths. Finally, these results collectively demonstrate the capacity of the cryogels to serve as a biocompatible bioadhesive that promotes cell adhesion, growth, and proliferation.

Injectability of optimized cryogels. Next, because cryogels were proven to be cytocompatible and biocompatible and due to the fact that the ultimate goal is to develop a material for minimally invasive deployment, the ability of cryogels to flow through a conventional-gauge needle, and then regain the original shapes once delivered was examined. Subject to shear stress during injection of cryogels experience a body force proportional to the applied pressure, resulting in the collapse of the polymeric network. Square-shaped HAGM and HPD cryogels were suspended in 0.2 mL of PBS and successfully syringe injected by means of an 18-gauge needle. The large volumetric change of the macroporous cryogels was presumably caused by a reversible collapse of the pores. After injection, deformed cryogels rapidly returned to their original undeformed configuration (shape recovery, 90%+), as surrounding water was reabsorbed into the gels.

Figure 9:
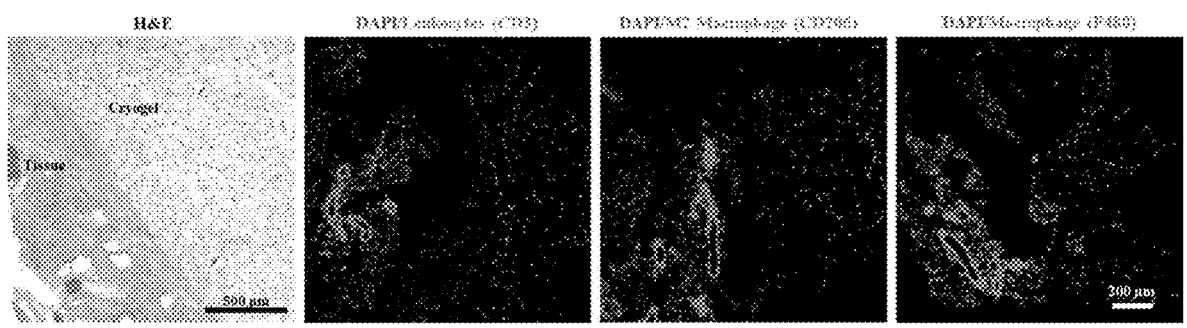
FIG. 9 contains images showing that injected HAGM and HPD cryogels showed high tissue integration with no immunocytotoxicity. Representative images of the HAGM and HPD cryogels. H&E staining of the HAGM and HPD sectioned cryogels after 21 days post-implantation. Fluorescent immunohistochemical analysis of subcutaneously injected HAGM and HPD cryogels showing no significant local lymphocyte infiltration (CD3) after 21 days and exhibiting some macrophages (CD206 and F408).
Figure 10:
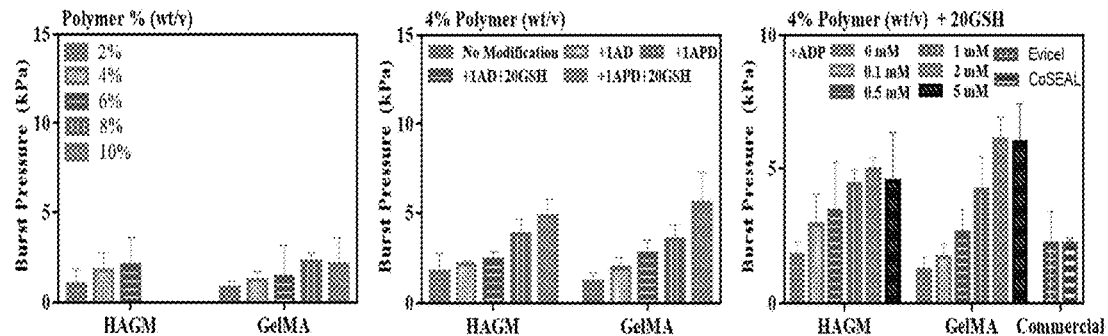
FIG. 10 is a series of bar graphs showing burst pressure.
Figure 11:
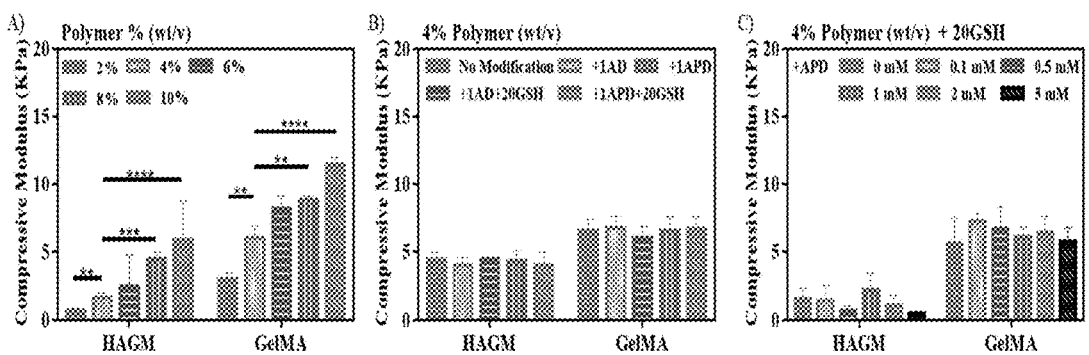
FIG. 11 is a series of bar graphs showing compression.
Figure 12:
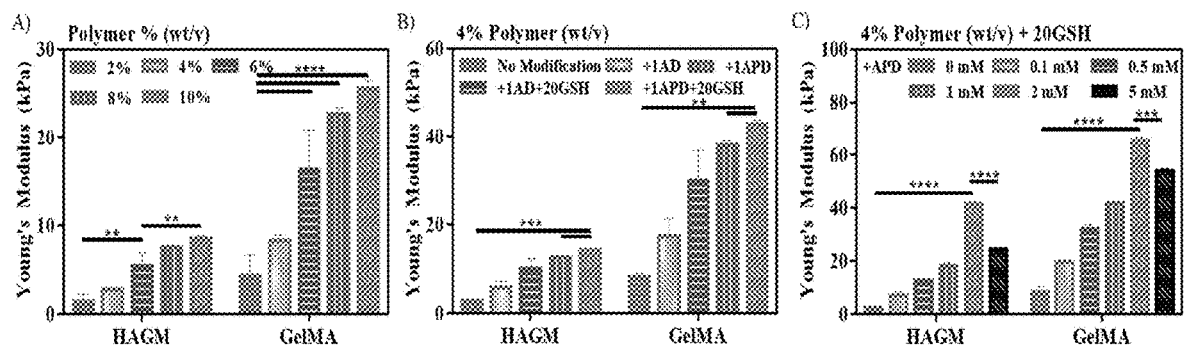
FIG. 12 is a series of bar graphs showing Young's Modulus.
Figure 13:
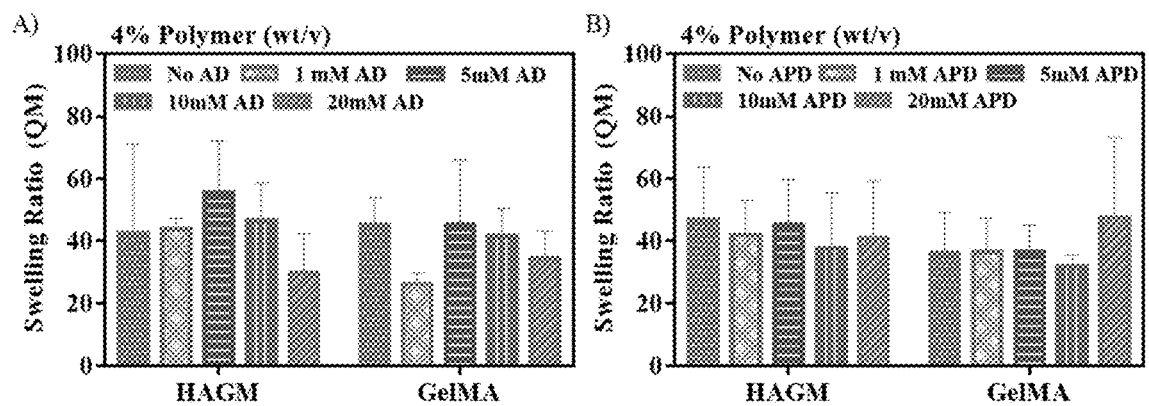
FIG. 13 is a series of bar graphs showing the swelling ratio.
Figure 14:
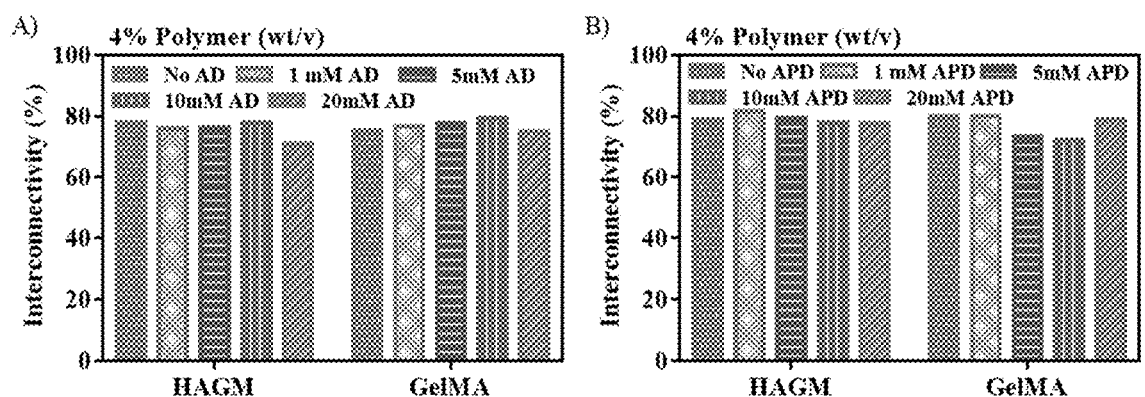
FIG. 14 is a series of bar graphs showing pore interconnectivity.
Figure 15:
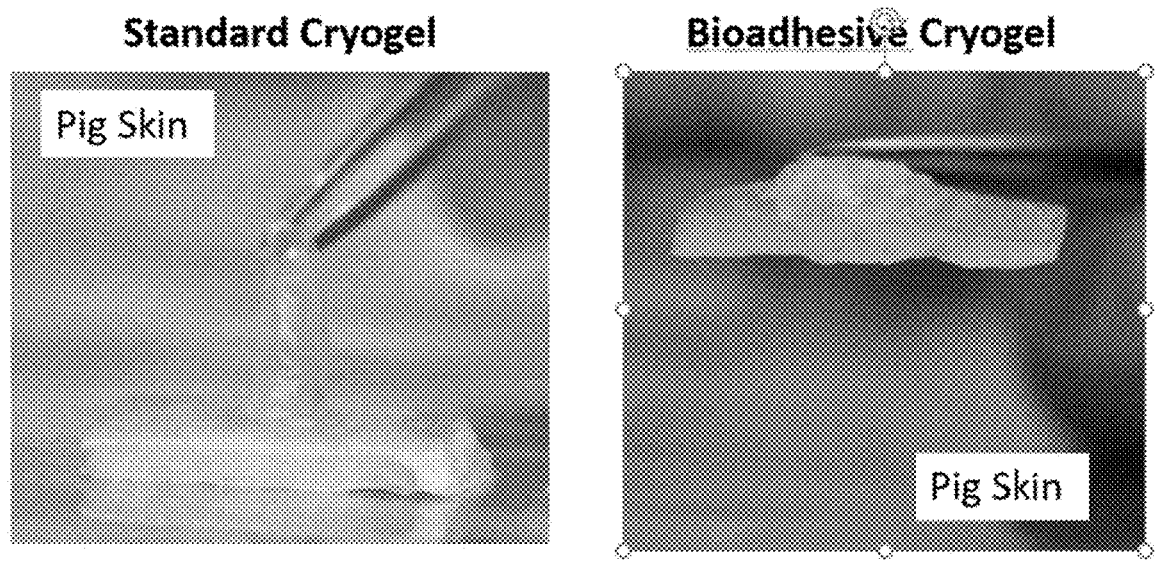
FIG. 15 contains images showing adhesion of a standard cryogel and a bioadhesive cryogel to pig skin.
Figure 16:
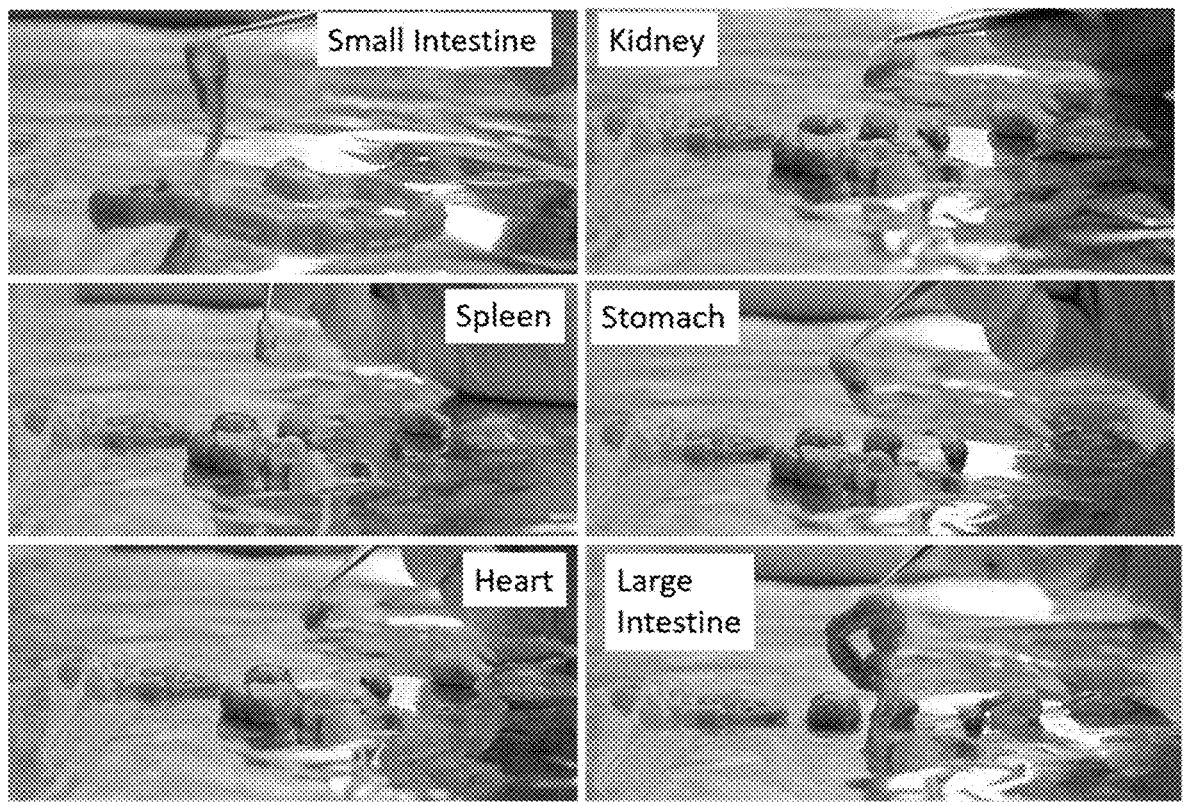
FIG. 16 contains images showing tissue adhesivity of bioadhesive cryogels in murine organs.

In vivo injectability, bioadhesion, and immunohistology. Lastly, we characterized the in vivo biodegradation of HAGM and HPD cryogels, including their interactions with native tissues via subcutaneous implantation in a murine animal model. Sterile composite cryogels (HAGM and HPD, 4×4×1 mm) were suspended in 0.2 mL of PBS and were injected subcutaneously in the backs of C57BL/6J mice. After 21 days post-implantation, the mice were euthanized prior to cryogel retrieval, along with adjacent tissue. Our results revealed no biodegradation of cryogels, as demonstrated by visual inspection. Explanted samples were then flash-frozen at an optimal cutting temperature (OCT) compound, cryosectioned into 14-µm slices, and mounted onto glass slides for histological examination. Hematoxylin and eosin (H&E) staining of the explanted samples revealed that the cryogels enabled migration of predominantly non-inflammatory cells (FIG. 9). These results confirmed that composite cryogels could be efficiently utilized in vivo for cell proliferation, migration, and tissue regeneration.

Cryosectioned samples were also analyzed through immunohistofluorescent staining of macrophage (CD206 and F480) and leukoctye (CD3) antigens (FIG. 9). Fluorescent images revealed negligible leukocyte infiltration 21 days post-implantation, as demonstrated by the absence of the red-fluorescent CD3 antigen. In contrast, macrophage infiltration was observed minimally at day 21 post-implantation, as demonstrated by the red-fluorescent CD206 and F480 antigens. We hypothesize that this inflammatory response was due to the surgical procedure used to deliver the samples to the subcutaneous pockets and is not associated with the material itself. However more time points and a longer study could be further conducted to explore the modulation of tissue responses at the injection/implantation site.

DISCUSSION

The results of this study suggest that a minimally invasive delivery approach can be used to introduce adhesive preformed shape-memory macroporous cryogels via needle-syringe injection into the body without mechanical deformations. These adhesive cryogels could be readily injected into the subcutaneous layer of the skin, used to fill in vivo tissue defects and cavities, or used as patches on internal or external organs, while the adhesive properties held tissues in place strongly. These materials have an interconnected macroporous architecture, which is advantageous with respect to their ability to facilitate cellular adhesion, infiltration, and tissue regeneration. Furthermore, this also offers a potential for the carrying of payloads (i.e. cells, drugs, nanoparticles) after devices are manufactured,[18] and would be of interest in future studies in conjugation with an adhesive motif. The most important requirement for these materials for minimally invasive therapies is the ability to be compressed up to 90%+ of its original volume, and reliably and quickly recover their original size and shape once placed in the body via the uptake of exudate. Shape memory allows for this function. Furthermore, the ability of these materials to reassume specific, predefined shapes after injection is likely to be useful in applications such as tissue patches (i.e. cardiac patches), ulcers, cartilage replacement, plastic surgery, fat replacement, oral surgeries, and voids left behind from tumor and tissue removals. Specifically, this is of interest where one desires a specific volume defect site, of a specific size and shape, to be filled with a single large biomaterial which can pull the tissue walls together. Alternatively, a large defect site with multiple smaller objects that pack in such a manner to leave voids that enhance diffusional transport to and from the objects and the host, and promote vascularization around each object.[23,24] Because of the ability to tune the adhesive properties by controlling conjugation of AD or APD, this can be achieved with fine control. Furthermore, the adhesive and extensible properties of these polymeric cryogel systems, which are also tunable, promote the attachment of the cryogel to surrounding tissues while the adhesive strength promotes tissue contraction and facilitates tissue regeneration—similar to the function of sutures or staples. Additionally, due to the minimally invasive delivery of these cryogels, no secondary surgical procedure is required to remove the cryogels, unlike sutures or staples, or secondary damage to surrounding tissues.

Cryogels have tissue-like robust mechanical properties due to a highly crosslinked polymer network which results from sterically entangled polymer chains, a high degree of chemical modification of HA or gelatin (or other biopolymers) and DOPA, and nearly complete reactivity of methacryoyl groups during cryogelation. Unlike their hydrogel counterpart, the unique macrostructural make up of cryogels presented here allow the cryogels to be compressed up to 90% of their original volume, resulting in injectable scaffolds. As has been previously explained, the water possessed within the pores of the cryogel can be expunged upon compression and then re-uptaken upon reversal of compression. This compression and release can be conducted without damage to the walls of the cryogel. However, it was noticed that beyond 90% compression, each incremental further compressive force applied create an inverse vacuum or suction affect which forces cryogel walls to "stick" together. Thereby taking a longer time to reuptake liquid once submerged. Furthermore, once all cryogel walls are fully collapsed any further compressive strain results in wall failure.

The cryogels have the ability to be created in any shape and size permanently. This shape and size are retained before and after compressive forces are applied without deformation or damage—shape memory. The relaxation is associated with the energy stored during the elastic cryogel collapse. The cryogels in this study were fabricated with low-molecular weight hyaluronic acid and gelatin but can be formed with a variety of materials, including other biopolymers highlighted in Table 1, as well as others. One could further tune their performance by altering their composition, formulation, and degradation profiles. The ability of these cryogels to be syringe delivered at a specific location without the need of an invasive surgery may decrease scarring, lessen the risk of infections, and reduce recovery times compared with traditional procedures, which typically require a secondary surgery or procedure or secondary sealants, staples, or sutures which damage surrounding tissue as well.

The maximum injectable cryogel size investigated to date is 8×8×1 mm for the square shaped cryogels. However, we were able to inject up to 10×10×1 mm (100 µL) square cryogels and up to D:8 mm and H:6 mm (300 µL) cylindrical cryogels. Furthermore, this technique used to fabricate cryogels is amenable to scaling up for larger injectable structures with larger gauge needles.

These cryogels can act as delivery vehicles for therapeutics and cells, with sustained release over time. By providing a protein drug depot at the size of an injection, the cryogels can potentially achieve high local protein concentrations without systemic exposure to the bioactive proteins. Biomacromolecules can be physically entrapped during polymerization, such as rhodamine-BSA for the pink hue necessary for better visualizations used here.

The acrylation of DOPA and PEG linker are techniques which can be scaled up and applied to other molecules as well. Herein, we described a motif in which DOPA was conjugated, thereby limiting its reactivity (autooxidative power) in solutions. This enabled DOPA to be grafted onto other acrylated biopolymers to enhance adhesion. Furthermore, we believe that adhesion was improved due to an increase in binding sites. This was achieved herein which is typically consumed in polydopamine.[21,25-27] This was further prevented by the incorporation of GSH to prevent oxidation, as our lab has previously shown. This dopamine oxidation prevention was then verified and tested for viability of cells which are sensitive to DOPA oxidation and resulted in 80%+viability of cell lines. Furthermore, it was shown that AD and APD grafted cryogels (HD, HPD, GD, GPD) did not exhibit any browning post-cryogelation indicating that oxidation was prevented.

REFERENCES

1. Su, K. & Wang, C. Recent advances in the use of gelatin in biomedical research. *Biotechnology Letters* 37, 2139-2145, (2015).
2. Spotnitz, W. D. Fibrin Sealant: Past, Present, and Future: A Brief Review. *World Journal of Surgery* 34, 632-634, (2010).
3. Radosevich, M., Goubran, H. A. & Burnouf, T. Fibrin Sealant: Scientific Rationale, Production Methods, Properties, and Current Clinical Use. *Vox Sanguinis* 72, 133-143, (1997).
4. Joch, C. The safety of fibrin sealants. *Cardiovascular Surgery* 11, 23-28, (2003).
5. Traver, M. A. & Assimos, D. G. New Generation Tissue Sealants and Hemostatic Agents: Innovative Urologic Applications. *Reviews in Urology* 8, 104-111 (2006).

6. Pascual, G. et al. Cytotoxicity of Cyanoacrylate-Based Tissue Adhesives and Short-Term Preclinical In Vivo Biocompatibility in Abdominal Hernia Repair. *PLoS ONE* 11, e0157920, (2016).
7. Hochberg, J., Meyer, K. M. & Marion, M. D. Suture Choice and Other Methods of Skin Closure. *Surgical Clinics of North America* 89, 627-641, (2009).
8. K., K. R. J. et al. A comparison of three methods of wound closure following arthroplasty. *The Journal of Bone and Joint Surgery. British volume* 88-B, 238-242, (2006).
9. Bencherif, S. A. et al. Injectable Cryogel-based Whole Cell Cancer Vaccines. *Nature communications* 6, 7556-7556, (2015).
10. Bencherif, S. A. et al. Influence of the degree of methacrylation on hyaluronic acid hydrogels properties. *Biomaterials* 29, 1739-1749, (2008).
11. Annabi, N. et al. Engineering a sprayable and elastic hydrogel adhesive with antimicrobial properties for wound healing. *Biomaterials* 139, 229-243, (2017).
12. F2458-05(2015), A. Standard test method for wound closure strength of tissue adhesives and sealants. *ASTM International* 13 (2015).
13. F2458-05(2015), A. Standard test method for burst strength of surgical sealants. *ASTM International* 12 (2015).
14. Kellett-Clarke, H., Stegmann, M., Barclay, A. N. & Metcalfe, C. CD44 Binding to Hyaluronic Acid Is Redox Regulated by a Labile Disulfide Bond in the Hyaluronic Acid Binding Site. *PLOS ONE* 10, e0138137, (2015).
15. Annabi, N. et al. Highly Elastic and Conductive Human-Based Protein Hybrid Hydrogels. *Adv Mater* 28, 40-49, (2016).
16. Bencherif, S. A., Sands, R. W., Koshy, S. T. & Mooney, D. J. Injectable cryogels for tumor vaccine delivery. US 2014/0227327 A1 (incorporated by reference).
17. Béduer, A. et al. A Compressible Scaffold for Minimally Invasive Delivery of Large Intact Neuronal Networks. *Advanced Healthcare Materials* 4, 301-312, (2015).
18. Bencherif, S. A. et al. Injectable preformed scaffolds with shape-memory properties. *Proceedings of the National Academy of Sciences of the United States of America* 109, 19590-19595, (2012).
19. Peach, R. H., Diane; Stamenkovic, Ivan; Aruffo, Alejandro. Identification of hyaluronic acid binding sites in the extracellular domain of CD44. *The Journal of Cell Biology* 122, 257-264 (1993).
20. Cui, F. Z., et al., Hyaluronic acid hydrogel immobilized with RGD peptides for brain tissue engineering. *Journal of Materials Science: Materials in Medicine* 17, 1393-1401, (2006)
21. Liebscher, J. et al. Structure of Polydopamine: A Never-Ending Story? *Langmuir: the ACS journal of surfaces and colloids* 29, 10539-10548, (2013).
22. Marini, J. J. Recruitment by sustained inflation: time for a change. *Intensive Care Medicine* 37, 1572, (2011).
23. Leor, J., Amsalem, Y. & Cohen, S. Cells, scaffolds, and molecules for myocardial tissue engineering. *Pharmacology & Therapeutics* 105, 151-163, (2005)
24. Halberstadt, C. et al. A Hydrogel Material for Plastic and Reconstructive Applications Injected into the Subcutaneous Space of a Sheep. *Tissue Engineering* 8, 309-319, (2002)
25. Munoz, P., Huenchuguala, S., Paris, I. & Segura-Aguilar, J. Dopamine Oxidation and Autophagy. Parkinson’s *Disease* 2012, 13, (2012)
26. Segura-Aguilar, J. & Paris, I. in *Handbook of Neurotoxicity* (ed Richard M. Kostrzewa) 865-883 (Springer New York, 2014)
27. Ding, Y. H., Floren, M. & Tan, W. Mussel-inspired polydopamine for bio-surface functionalization. *Biosurface and Biotribology* 2, 121-136, (2016)

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of formula (I), or a pharmaceutically acceptable salt thereof:

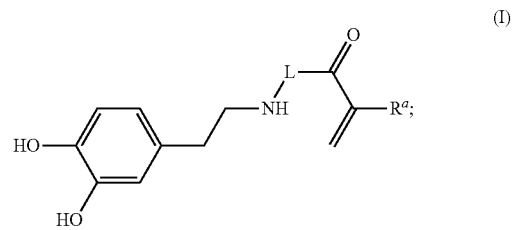

wherein L represents a polymeric linking moiety; and $R^a$ represents H, $(C_1-C_6)$alkyl, or phenyl.

2. The compound of claim 1, wherein L represents a hydrophilic linear polymeric linking moiety.

3. The compound of claim 1, wherein L represents a polyethylene glycol linking moiety.

4. The compound of claim 1, selected from the group consisting of:

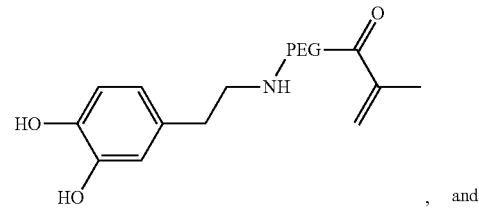

, and

-continued

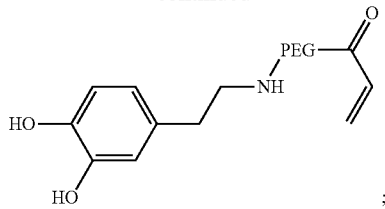

wherein PEG is a polyethylene glycol linker.

5. A cryogel, comprising:
a residue of a compound of claim 1; and
a hydrophilic bio-compatible polymer.

6. The cryogel of claim 5, wherein the residue of a compound of claim 3 is crosslinked to the hydrophilic bio-compatible polymer.

7. The cryogel of claim 5, wherein the hydrophilic bio-compatible polymer is selected from the group consisting of a gelatin-based bio-compatible polymer and a hyaluronic acid-based bio-compatible polymer.

8. The cryogel of claim 7, wherein the hydrophilic bio-compatible polymer is a gelatin-based bio-compatible polymer; and the gelatin-based bio-compatible polymer is methacrylated gelatin (GelMA).

9. The cryogel of claim 7, wherein the hydrophilic bio-compatible polymer is a hyaluronic acid-based bio-compatible polymer; and the hyaluronic acid-based bio-compatible polymer is hyaluronic acid methacrylate (HAGM).

10. The cryogel of claim 5, wherein the concentration of the hydrophilic bio-compatible polymer in the cryogel is about 0.5% wt/v to about 25% wt/v; about 0.5% wt/v to about 10% wt/v; about 2% wt/v to about 6% wt/v; about 3% wt/v to about 5% wt/v; or about 4% wt/v.

11. The cryogel of claim 5, wherein the concentration of the residue of a compound of claim 3 is about 0.1 mM to about 5.0 mM; about 0.5 mM to about 3.0 mM; about 1.0 mM to about 2.5 mM; or about 2.0 mM.

12. The cryogel of claim 5, further comprising an anti-oxidant.

13. A formulation, comprising a cryogel of claim 5 and a pharmaceutically acceptable carrier.

* * * * *